(12) United States Patent
Alig et al.

(10) Patent No.: US 8,173,641 B2
(45) Date of Patent: May 8, 2012

(54) 4-AMINO-1,2,3-BENZOXATHIAZINE-DERIVATIVES AS PESTICIDES

(75) Inventors: Bernd Alig, Königswinter (DE);
Klaus-Helmut Müller, Düsseldorf (DE);
Eva-Maria Franken, Lyons (FR);
Ulrich Görgens, Ratingen (DE); Arnd Voerste, Köln (DE)

(73) Assignee: Bayer CropScience AG, Monheim (DE)

(*) Notice: Subject to any disclaimer, the term of this patent is extended or adjusted under 35 U.S.C. 154(b) by 198 days.

(21) Appl. No.: 12/654,177

(22) Filed: Dec. 11, 2009

(65) Prior Publication Data

US 2010/0267703 A1    Oct. 21, 2010
US 2011/0118240 A2    May 19, 2011

(30) Foreign Application Priority Data

Dec. 15, 2008 (EP) .................................. 08171681

(51) Int. Cl.
C07D 291/08 (2006.01)
A01N 43/88 (2006.01)

(52) U.S. Cl. ........................................ 514/222.8; 544/2
(58) Field of Classification Search .... 544/2; 514/222.8
See application file for complete search history.

(56) References Cited

U.S. PATENT DOCUMENTS

| | | |
|---|---|---|
| 2,842,476 A | 7/1958 | Schreiber |
| 3,317,523 A | 5/1967 | Wright |
| 3,780,030 A | 12/1973 | Morris |
| 4,844,734 A | 7/1989 | Iwasaki et al. |
| 4,888,049 A | 12/1989 | Iwasaki et al. |
| 4,925,864 A | 5/1990 | Inamori et al. |
| 5,385,927 A | 1/1995 | Michel et al. |
| 5,462,912 A | 10/1995 | Hioki et al. |
| 5,538,937 A | 7/1996 | Hasebe et al. |
| 5,705,476 A | 1/1998 | Hoffarth |
| 5,792,755 A | 8/1998 | Sagenmüller et al. |
| 5,863,929 A | 1/1999 | Klimkowski et al. |
| 6,602,823 B1 | 8/2003 | Röchling et al. |
| 6,645,914 B1 | 11/2003 | Woznica et al. |
| 2003/0224939 A1 | 12/2003 | Miles |
| 2005/0009880 A1 | 1/2005 | Cottrell et al. |
| 2005/0096386 A1 | 5/2005 | Cottrell et al. |
| 2006/0052374 A1 | 3/2006 | Carroll et al. |
| 2008/0319081 A1 | 12/2008 | Fischer et al. |
| 2009/0093544 A1 | 4/2009 | Fischer et al. |
| 2009/0105235 A1 | 4/2009 | Jeschke et al. |
| 2009/0149506 A1 | 6/2009 | Funke et al. |
| 2009/0209513 A1 | 8/2009 | Fischer et al. |

FOREIGN PATENT DOCUMENTS

| | | |
|---|---|---|
| CA | 1 162 071 | 2/1984 |
| DE | 33 39 344 A1 | 5/1985 |
| EP | 0 036 106 A2 | 9/1981 |
| EP | 0 353 631 A2 | 2/1990 |
| EP | 0 453 086 A2 | 10/1991 |
| EP | 0 626 372 A1 | 11/1994 |
| EP | 0 664 081 A2 | 7/1995 |
| EP | 0 681 865 A2 | 11/1995 |
| FR | 2 600 494 | 12/1987 |
| WO | WO 92/16108 A1 | 10/1992 |
| WO | WO 95/17817 A1 | 7/1995 |
| WO | WO 97/37967 A1 | 10/1997 |
| WO | WO 97/49404 A1 | 12/1997 |
| WO | WO 98/35553 A1 | 8/1998 |
| WO | WO 00/35278 A1 | 6/2000 |
| WO | WO 03/047517 A2 | 6/2003 |
| WO | WO 2007/030582 A2 | 3/2007 |
| WO | WO 2007/068350 A1 | 6/2007 |
| WO | WO 2007/068355 A1 | 6/2007 |
| WO | WO 2007/068356 A1 | 6/2007 |
| WO | WO 2007/068357 A1 | 6/2007 |
| WO | WO 2007/068428 A2 | 6/2007 |
| WO | WO 2007/089646 A1 | 8/2007 |

OTHER PUBLICATIONS

Baur, P., et al., "Polydisperse Ethoxylated Fatty Alcohol Surfactants as Accelerators of Cuticular Penetration. 1. Effects of Ethoxy Chain Length and the Size of the Penetrants," *Pestic. Sci.* 51:131-152, John Wiley & Sons, Inc., Great Britain (1997).

Böshagen, H., "Über 3-Chlor-1.2-benzisoxazole," *Chem. Ber.* 100:3326-3330, Germany (1967).

Bozó, E., et al., "New 1,5-Diaryl-3-(substituted amino)-1H-1,2,4-triazoles as Anti-inflammatory Agents," *Arch. Pharm.* 355:583-587, VCH Verlagsgesellschaft mbH, Germany (1989).

Giumanini, A.G., et al., "N-Permethylation of Primary and Secondary Aromatic Amines," *Synthesis* 1980(9):743-746, Georg Thieme Verlag KG, USA (1980).

Kamal, A., et al., "Efficient Enzymatic Cyclization of 2-(Carbamoyloxy)- and 2-(Sulfamoyloxy)-Benzonitriles by Ultrasonically Stimulated Bakers' Yeast," *Heterocycles* 31:577-579, The Japan Institute of Heterocyclic Chemistry, Japan (1990).

Lam, P.Y.S., et al., "Structure-based Design of Novel Guanidine/Benzamidine Mimics: Potent and Orally Bioavailable Factor Xa Inhibitors as Novel Anticoagulants," *J. Med Chem.* 46:4405-4418, American Chemical Society, USA (2003).

Liberman, S., et al., "Synthèse d'amidines de l'acide salicylique," *Bull. Soc. Chim. Fr.* 687:185-187, France (1958).

(Continued)

Primary Examiner — Kahsay T Habte
(74) Attorney, Agent, or Firm — Sterne, Kessler, Goldstein & Fox P.L.L.C.

(57) ABSTRACT

The present invention relates to novel benzoxathiazine derivatives of the formula (I)

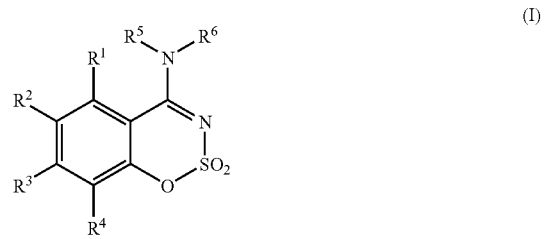

in which $R^1$, $R^2$, $R^3$, $R^4$, $R^5$ and $R^6$ are each as defined in the description, to several processes for preparation thereof and to the use thereof as insecticides and/or acaricides in combination with further compositions such as penetrants and/or ammonium or phosphonium salts.

12 Claims, No Drawings

OTHER PUBLICATIONS

Linusson, A., et al., "Statistical Molecular Desgin, Parrallel Synthesis, and Biological Evaluation of a Library of Thrombin Inhibitors," *J. Med. Chem.* 44:3424-3439, American Chemical Society, USA (2001).

Lohaus, G., "Dartellung und Umsetzungen von Aryloxysulfonylisocyanaten," *Chem. Ber 105*:2791-2799, Germany (1972).

Palermo, M.G., "Novel One-pot Cyclization of *Ortho* Substituted Benzonitriles to 3-Amino-1,2-benzisoxazoles," *Tetrahedron Lett.* 37:2885-2886, Elsevier Science Ltd., Great Britain (1996).

Schröter, M., "Bis(pyrazolyl)- und Bis(1,2,4)triazolyl-Schwefel-Derivate," *Z. Anorg. Allg. Chem. 629*:1300-1307, Wiley-VCH Verlag GmbH & Co. KGaA, Germany (2003).

Siiutske, G.M., and Kapples, K.J., "A Novel Synthesis of 3-Amino-1,2-benzisoxazoles—an Entry into the Isoxazolo[3,4,5-*ef*][1,4]benzoxazepine Ring System," *J. Heterocyclic Chem. 26*:1293-1298, USA (1989).

International Search Report for International Application No. PCT/EP2009/008581, European Patent Office, Rijswijk, Netherlands, mailed on Feb. 16, 2010.

4-AMINO-1,2,3-BENZOXATHIAZINE-DERIVATIVES AS PESTICIDES

The present invention relates to novel pesticides, to several processes for preparation thereof and to the use thereof as active ingredients, especially the use thereof as insecticides and/or acaricides.

Some 4-amino-1,2,3-benzoxathiazine derivatives are described in the literature. 4-Amino-1,2,3-benzoxathiazine 2,2-dioxide (CAS Registry No.: 129661-85-4) is described in Heterocycles, Vol. 31, 4, 577-579 (1990) and 4-amino-5-methoxy-N-(2-methyl-2-phenylpropyl)-1,2,3-benzoxathiazine 2,2-dioxide (CAS Registry No.: 929022-83-3) in WO 2007/030582. Neither publication reports insecticidal, acaricidal or nematicidal action.

The literature likewise already states that the action of various active ingredients can be enhanced by adding further compositions, including ammonium salts. These are, however, detergent salts (e.g. WO 95/017817) or salts with relatively long alkyl and/or aryl substituents, which have permeabilizing action or increase the solubility of the active ingredient (e.g. EP-A 0 453 086, EP-A 0 664 081, FR-A 2 600 494, U.S. Pat. Nos. 4,844,734, 5,462,912, 5,538,937, US-A 03/0224939, US-A 05/0009880, US-A 05/0096386). Moreover, the prior art describes the effect only for particular active ingredients and/or particular applications of the corresponding compositions. In other cases again, the salts are those of sulphonic acids, in which the acids themselves have a paralysing effect on insects (U.S. Pat. No. 2,842,476). An enhancement of action, for example by ammonium sulphate, has also been described, for example, for the herbicides glyphosate and phosphinothricin (U.S. Pat. No. 6,645,914, EP-A2 0 036 106). The use of ammonium sulphate as a formulating assistant has likewise been described for particular active ingredients and applications (WO 92/16108), but serves there to stabilize the formulation, not to enhance the action. In addition, combinations of ammonium salts with active insecticidal ingredients are described in WO 07/068356, WO 07/068428, WO 07/068355, WO 07/068357, and WO 07/068350. Explicit reference is hereby made to these publications.

It is an object of the present invention to provide aminobenzoxathiazine derivatives which can be used as insecticides and/or acaricides, especially with a satisfactory insecticidal and/or acaricidal action against animal pests, against a broad spectrum of animal pests, with a high selectivity and good compatibility in useful plant crops, and which can be used in combination with further compositions for improving efficacy, especially against insects and spider mites which are difficult to control.

Novel 4-amino-1,2,3-benzoxathiazine derivatives of the general formula (I)

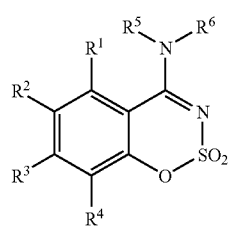

(I)

have been found, in which
$R^1$, $R^2$, $R^3$ and $R^4$ are each independently selected from the group consisting of
hydrogen, halogen, carbamoyl, thiocarbamoyl, nitro, cyano, hydroxyl, $SF_5$, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_6$-alkoxy, $C_1$-$C_6$-alkoxycarbonyl, $C_3$-$C_6$-alkenyloxy, $C_3$-$C_6$-cycloalkyloxy, $C_3$-$C_6$-cycloalkyloxy-$C_1$-$C_4$-alkyl, $C_1$-$C_4$-alkoxy-$C_1$-$C_4$-alkyl, aryloxy, hetaryloxy, aryl-$C_1$-$C_4$-alkyloxy, hetaryl-$C_1$-$C_4$-alkyloxy, O-acetyl, ($C_1$-$C_4$-alkyl)amino, di-($C_1$-$C_4$-alkyl)amino, $C_3$-$C_6$-trialkylsilyl, aryl, hetaryl, aryl-$C_1$-$C_6$-alkyl and hetaryl-$C_1$-$C_6$-alkyl,
where these radicals may be unsubstituted or may bear one, two or more radicals from the group of
halogen, cyano, $C_1$-$C_6$-alkyl, $C_3$-$C_8$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;
$R^5$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_8$-alkyl, $C_3$-$C_6$-cycloalkyl, $C_2$-$C_6$-alkenyl, $C_1$-$C_4$-alkoxy, $C_1$-$C_4$-alkylthio, $C_1$-$C_4$-alkylsulphinyl, $C_1$-$C_4$-alkylsulphonyl, aryl, hetaryl, aryl-$C_1$-$C_6$-alkyl, hetaryl-$C_1$-$C_6$-alkyl and —(C=X)NR$^7$R$^{7'}$,
where these radicals may be unsubstituted or may bear one, two or more radicals from the group of
halogen, cyano, $C_1$-$C_6$-alkyl, $C_3$-$C_8$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;
$R^6$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_8$-alkyl, $C_3$-$C_6$-cycloalkyl, $C_2$-$C_6$-alkenyl, $C_1$-$C_4$-alkylsulphinyl, $C_1$-$C_4$-alkylsulphonyl, aryl, hetaryl, aryl-$C_1$-$C_6$-alkyl, hetaryl-$C_1$-$C_6$-alkyl and —(C=X)NR$^7$R$^{7'}$,
where these radicals may be unsubstituted or may bear one, two or more radicals from the group of
halogen, cyano, $C_1$-$C_6$-alkyl, $C_3$-$C_8$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;
where $R^5$, $R^6$ together are not phenylbutyl and hydrogen if $R^1$ is methoxy;
where the $R^1$, $R^2$, $R^3$, $R^4$ radicals are not all hydrogen if $R^5$ and $R^6$ are hydrogen;
$R^7$ is selected from the group consisting of $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, aryl, hetaryl,
where these radicals may be unsubstituted or may bear one, two or more radicals from the group of
halogen, cyano, nitro, $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy;
$R^{7'}$ is selected from the group consisting of hydrogen, $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, aryl, hetaryl,
where these radicals may be unsubstituted or may bear one, two or more radicals from the group of
halogen, cyano, nitro, $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy;
X is O, S,
and salts of compounds of the formula (I).

Likewise found has been good insecticidal action of a compound of the formula (I) where the $R^1$, $R^2$, $R^3$, $R^4$, $R^5$ and $R^6$ radicals are all hydrogen.

Some of the compounds of the formula (I) may be present in different polymorphic forms or as a mixture of different polymorphic forms. Both the pure polymorphs and the polymorph mixtures form part of the subject-matter of the invention and can be used in accordance with the invention.

Some of the compounds of the formula (I) include diastereomers or enantiomers.

The inventive 4-amino-1,2,3-benzoxathiazines are defined in general terms by the formula (I). Preferred radical definitions of the formulae above and specified hereinafter are given below. These definitions apply equally to the end products of the formula (I) and to all intermediates.

A first embodiment of the present invention encompasses compounds of the general formula (I) in which $R^1$, $R^2$, $R^3$ and $R^4$ are preferably each independently selected from the group consisting of
hydrogen, halogen, cyano, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_4$-alkylthio, $C_1$-$C_4$-haloalkyl, $C_1$-$C_4$-alkylcarbonyl, $C_1$-$C_6$-alkoxy, $C_1$-$C_6$-alkoxycarbonyl, $C_3$-$C_6$-alkenyloxy, $C_3$-$C_6$-cycloalkyloxy, $C_3$-$C_6$-cycloalkyloxy-$C_1$-$C_4$-alkyl, $C_1$-$C_4$-haloalkoxy, $C_1$-$C_4$-alkoxy-$C_1$-$C_4$-alkyl, O-acetyl, aryl, hetaryl, aryl-$C_1$-$C_6$-alkyl, hetaryl-$C_1$-$C_6$-alkyl, and from optionally $C_1$-$C_6$-alkyl-substituted aryloxy, hetaryloxy, aryl-$C_1$-$C_4$-alkyloxy, hetaryl-$C_1$-$C_4$-alkyloxy,
where the $R^1$, $R^2$, $R^3$ and $R^4$ radicals are not all hydrogen if $R^5$ and $R^6$ are hydrogen;

$R^1$, $R^2$, $R^3$ and $R^4$ are more preferably each independently selected from the group consisting of hydrogen, halogen, cyano, $C_1$-$C_3$-alkyl, $C_1$-$C_3$-haloalkyl, $C_1$-$C_3$-alkoxy, $C_1$-$C_2$-haloalkoxy, $C_1$-$C_4$-alkoxy-$C_1$-$C_4$-alkyl, $C_1$-$C_4$-alkoxycarbonyl, O-acetyl, and from optionally $C_1$-$C_6$-alkyl-substituted aryloxy, hetaryloxy, aryl-$C_1$-$C_2$-alkyloxy, hetaryl-$C_1$-$C_2$-alkyloxy,
where the $R^1$, $R^2$, $R^3$ and $R^4$ radicals are not all hydrogen if $R^5$ and $R^6$ are hydrogen;

$R^1$, $R^2$, $R^3$ and $R^4$ are even more preferably each independently selected from the group consisting of hydrogen, methoxy, ethoxy, cyano, fluorine, chlorine, methyl, ethyl, bromine, trifluoromethyl, $OCHF_2$, $OCF_3$ and $OCClF_2$, imidazolyl, methylbenzyloxy,
where the $R^1$, $R^2$, $R^3$ and $R^4$ radicals are not all hydrogen if $R^5$ and $R^6$ are hydrogen;

$R^1$, $R^2$, $R^3$ and $R^4$ are especially preferably each independently selected from the group consisting of hydrogen, methoxy, ethoxy, fluorine, chlorine, bromine, methyl, trifluoromethyl, $OCHF_2$,
where the $R^1$, $R^2$, $R^3$ and $R^4$ radicals are not all hydrogen if $R^5$ and $R^6$ are hydrogen.

A second embodiment of the present invention encompasses compounds of the general formula (I) in which $R^5$ is preferably selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_6$-alkyl, $C_3$-$C_6$-cycloalkyl, $C_2$-$C_6$-alkenyl, $C_1$-$C_4$-alkoxy, $C_1$-$C_4$-haloalkyl, $C_1$-$C_4$-haloalkoxy, aryl, hetaryl, aryl-$C_1$-$C_2$-alkyl, hetaryl-$C_1$-$C_2$-alkyl, ($C_1$-$C_4$-haloalkyl)carbonyl, —(C=X)$NR^7R^{7\prime}$, $R^5$ is more preferably selected from the group consisting of hydrogen, ($C_1$-$C_3$-alkyl)carbonyl, ($C_1$-$C_3$-alkoxy)carbonyl, $C_1$-$C_4$-alkyl, $C_1$-$C_4$-alkoxy, $C_1$-$C_4$-haloalkyl, $C_1$-$C_4$-haloalkoxy, aryl-$C_1$-$C_2$-alkyl, hetaryl-$C_1$-$C_2$-alkyl, ($C_1$-$C_4$-haloalkyl)carbonyl, —(C=X)$NR^7R^{7\prime}$, $R^5$ is even more preferably selected from the group consisting of hydrogen, methyl, ethyl, isopropyl, methoxycarbonyl, ethoxycarbonyl, acetyl and trifluoroacetyl, $R^5$ is especially preferably hydrogen, methyl;

$R^7$ is preferably selected from the group consisting of $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl, thiophene, furan,
where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

$R^7$ is more preferably selected from the group consisting of $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl,
where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

$R^{7\prime}$ is preferably selected from the group consisting of hydrogen, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl, thiophene, furan,
where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

$R^{7\prime}$ is more preferably selected from the group consisting of hydrogen, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl,
where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

X is preferably and more preferably O.

A third embodiment of the present invention encompasses compounds of the general formula (I) in which $R^6$ is preferably selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_6$-alkyl, $C_3$-$C_6$-cycloalkyl, $C_2$-$C_6$-alkenyl, $C_1$-$C_4$-haloalkyl, aryl, hetaryl, aryl-$C_1$-$C_2$-alkyl, hetaryl-$C_1$-$C_2$-alkyl, ($C_1$-$C_4$-haloalkyl)carbonyl, —(C=X)$NR^7R^{7\prime}$, $R^6$ is more preferably selected from the group consisting of hydrogen, ($C_1$-$C_3$-alkyl)carbonyl, ($C_1$-$C_3$-alkoxy)carbonyl, $C_1$-$C_4$-alkyl, $C_1$-$C_4$-haloalkyl, aryl-$C_1$-$C_2$-alkyl, hetaryl-$C_1$-$C_2$-alkyl, ($C_1$-$C_4$-haloalkyl)carbonyl, —(C=X)$NR^7R^{7\prime}$, $R^6$ is even more preferably selected from the group consisting of hydrogen, methyl, ethyl, isopropyl, methoxycarbonyl, ethoxycarbonyl, acetyl and trifluoroacetyl;

$R^6$ is especially preferably hydrogen.

$R^7$ is preferably selected from the group consisting of $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl, thiophene, furan,
where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

$R^7$ is more preferably selected from the group consisting of $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl, where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

$R^{7'}$ is preferably selected from the group consisting of hydrogen, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl, thiophene, furan,
where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

$R^{7'}$ is more preferably selected from the group consisting of hydrogen, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl,
where these radicals may be unsubstituted or may bear one, two or more radicals from the group of
halogen, cyano, nitro, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy;

X is preferably and more preferably O.

In the context of these embodiments of the present invention, it is possible to combine the individual general, preferred, more preferred, even more preferred and especially preferred definitions for the substituents $R^1$ to $R^6$ with one another as desired. This means that the present invention encompasses compounds of the general formula (I) in which, for example, the substituent $R^1$ has a preferred definition and the substituents $R^5$ and $R^6$ have the general definition, or else, for example, the substituent $R^2$ has a preferred definition, the substituent $R^3$ has a more preferred definition, and the remaining substituents have the general definition. These individual combinations are not specified expressis verbis for reasons of clarity, but are considered to be encompassed within the scope of the present invention.

The present invention preferably also provides the lithium, sodium, potassium, magnesium, calcium, ammonium, $C_1$-$C_4$-alkylammonium, di-($C_1$-$C_4$-alkyl)ammonium, tri-($C_1$-$C_4$-alkyl)ammonium, tetra-($C_1$-$C_4$-alkyl)ammonium, tri-($C_1$-$C_4$-alkyl)sulphonium, $C_5$- or $C_6$-cycloalkylammonium, di-($C_1$-$C_2$-alkyl)benzylammonium and tri-($C_1$-$C_2$-alkyl)benzylammonium salts of compounds of the formula (I) in which $R^1$ to $R^6$ have the above general, preferred, more preferred and especially preferred definitions and which can be prepared by generally customary processes.

The compounds of the general formula (I) may additionally optionally form salts by addition of a suitable inorganic or organic acid, for example HCl, HBr, $H_2SO_4$ or $HNO_3$, but also oxalic acid or sulphonic acids, onto a basic group, for example amino or alkylamino. Suitable substituents present in deprotonated form, for example sulphonic acids or carboxylic acids, can form internal salts with groups which are themselves protonatable, such as amino groups. Salts can likewise be formed in the case of suitable substituents, for example sulphonic acids or carboxylic acids, by virtue of the hydrogen being replaced by a cation suitable in the agrochemical sector. These salts are, for example, metal salts, especially alkali metal salts or alkaline earth metal salts, especially sodium and potassium salts, or else ammonium salts, salts with organic amines or quaternary ammonium salts with cations of the formula [NRR'R''R''']$^+$ in which R to R''' are each independently an organic radical, especially alkyl, aryl, aralkyl or alkylaryl.

In the general formula (I) and all other formulae in the present invention, the alkyl, alkoxy, haloalkyl, alkoxyalkyl, alkenyl, alkynyl, haloalkoxy, alkylamino, dialkylamino, alkylthio and haloalkylthio radicals, and the corresponding unsaturated and/or substituted radicals in the carbon skeleton may each be straight-chain or branched. Unless stated specifically, the lower carbon skeletons, for example having 1 to 6 carbon atoms, especially 1 to 4 carbon atoms, or in the case of unsaturated groups having 2 to 6 carbon atoms, especially 2 to 4 carbon atoms, are preferred for these radicals. Alkyl radicals, also in the combined definitions such as alkoxy, haloalkyl, etc., are, for example, methyl, ethyl, propyls such as n- or i-propyl, butyls such as n-, iso- or tert-butyl, pentyls such as n-pentyl, isopentyl or neopentyl, hexyls such as n-hexyl, i-hexyl, 3-methylpentyl, 2,2-dimethylbutyl or 2,3-dimethylbutyl, heptyls, such as n-heptyl, 1-methylhexyl or 1,4-dimethyl-pentyl; alkenyl and alkynyl radicals are defined as the possible unsaturated radicals corresponding to the alkyl radicals, where at least one double bond or triple bond, preferably one double bond or triple bond, is present. Alkenyl is, for example, vinyl, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, ethynyl, propargyl, but-2-yn-1-yl, but-3-yn-1-yl and 1-methylbut-3-yn-1-yl.

When haloalkyl groups and haloalkyl radicals of haloalkoxy, haloalkylthio, haloalkenyl, haloalkynyl, inter alia, are specified, the lower carbon skeletons, for example having 1 to 6 carbon atoms or 2 to 6, especially 1 to 4 carbon atoms or preferably 2 to 4 carbon atoms, are preferred for these radicals, as are the corresponding unsaturated and/or substituted radicals in the carbon skeleton, in each case straight-chain or branched. Examples are difluoromethyl, 2,2,2-trifluoroethyl, trifluoroallyl, 1-chloroprop-1-yl-3-yl.

Halogen is fluorine, chlorine, bromine or iodine. Haloalkyl, -alkenyl and -alkynyl are, respectively, alkyl, alkenyl and alkynyl partly or fully substituted by halogen, preferably by fluorine, chlorine or bromine, especially by fluorine and/or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

The present compounds of the general formula (I) may optionally have a chiral carbon atom. Corresponding chiral carbon atoms may occur especially in the $R^5$ and $R^6$ substituents.

According to the Cahn Ingold Prelog (CIP) Rules, these substituents may have either an (R) or an (S) configuration.

The present invention encompasses compounds of the general formula (I) both with (S) and with (R) configuration at the particular chiral carbon atoms, which means that the present invention includes the compounds of the general formula (I) in which the carbon atoms in question each independently have
(1) (R) configuration; or
(2) (S) configuration.

When more than one chiral centre is present in the compounds of the general formula (I), any desired combinations of the configurations of the chiral centres are possible, which means that
(1) one chiral centre has the (R) configuration and the other chiral centre the (S) configuration;
(2) one chiral centre has the (R) configuration and the other chiral centre the (R) configuration; and
(3) one chiral centre has the (S) configuration and the other chiral centre the (S) configuration.

Preparation of the Inventive Compounds of the General Formula (I)

The present invention further provides processes for preparing corresponding compounds of the general formula (I) and/or salts thereof.

In a first embodiment (A) of the present invention, the compounds of the general formula (I) are prepared by cyclizing 2-cyanophenyloxysulphonamides of the general formula (II) in which $R^1$, $R^2$, $R^3$ and $R^4$ are each as defined above in the presence of ultrasound-pretreated baker's yeast to give 4-amino-1,2,3-benzoxathiazine derivatives of the general formula (I)

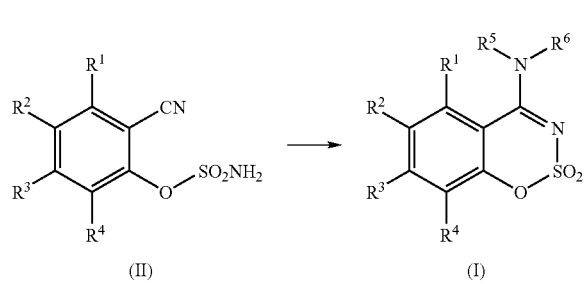

(II)    (I)

where $R^1$, $R^2$, $R^3$ and $R^4$ are each as defined above and $R^5$ and $R^6$ are each hydrogen; cf. Heterocycles, Vol. 31, No. 4, 577-579 (1990).

In a second embodiment (B) of the present invention, the compounds of the general formula (I) are prepared by reacting 2-cyanophenols of the general formula (III) in which $R^1$, $R^2$, $R^3$ and $R^4$ are each as defined above by known methods (cf. Chemische Berichte 105(9), 2791-9 (1972)) with chlorosulphonyl isocyanate to give 2-cyanophenyloxysulphonamides of the general formula (II) which are cyclized, without further isolation, under the reaction conditions, to give 4-amino-1,2,3-benzoxathiazine derivatives of the general formula (I)

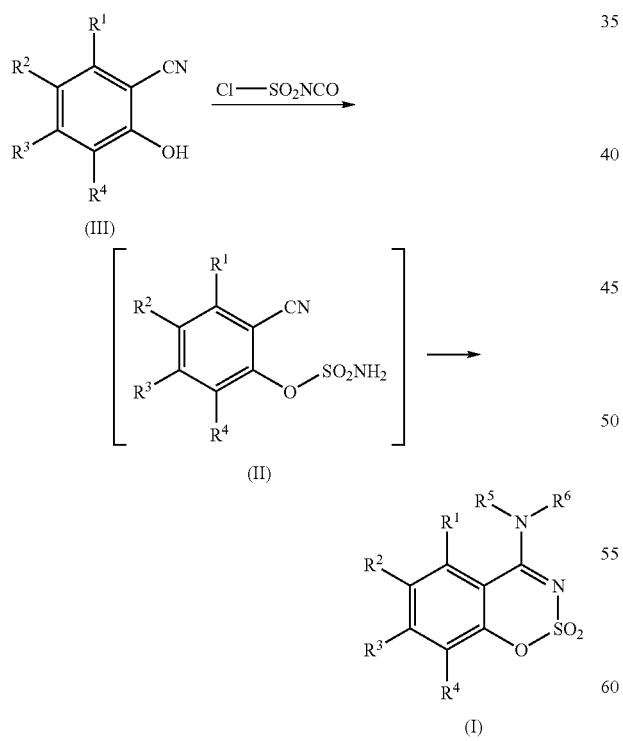

where $R^1$, $R^2$, $R^3$ and $R^4$ are each as defined above and $R^5$ and $R^6$ are each hydrogen.

In a third embodiment (C) of the present invention, the compounds of the general formula (I) are prepared by reacting 2-amidinophenols of the general formula (IV) in which $R^1$, $R^2$, $R^3$, $R^4$, $R^5$ and $R^6$ are each as defined above with a sulphonyl derivative of the general formula (V), where X and Y are each a leaving group such as halogen, pyrazole, triazole or imidazole; cf. WO 2007/030582:

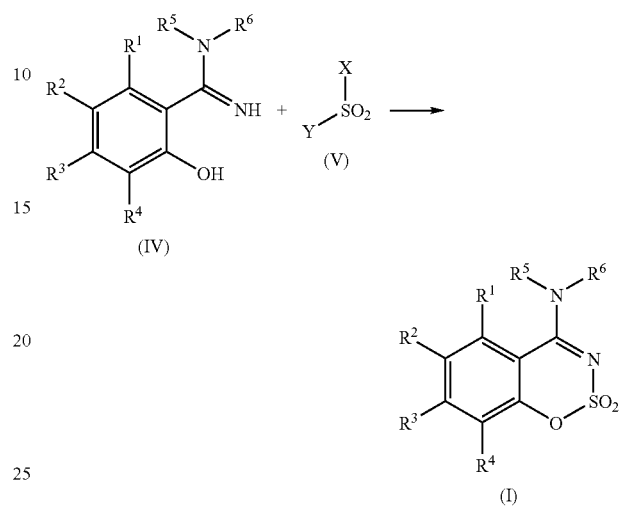

Sulphonyl derivatives of the general formula (V) are known (cf. Zeitschrift für Anorganische and Allgemeine Chemie 629 (7-8), 1300-1307 (2003)) or commercially available (1,1'-sulphonylbis-1H-1,2,4-triazole: Florida Center for Heterocyclic Compounds, Department of Chemistry, University of Florida, P O Box 117200, Gainesville, Fla., 32611-7200, USA; 1,1'-sulphonyldiimidazole: Sigma-Aldrich, P O Box 14508, St. Louis, Mo., 63178, USA).

Furthermore, in the third embodiment (C) of the present invention, the compounds of the general formula (Ia) are prepared by reacting 2-amidinophenols of the general formula (IVa) in which $R^2$, $R^3$, $R^4$, $R^5$ and $R^6$ are each as defined above and $R^1$ is fluorine with a sulphonyl derivative of the formula (Va):

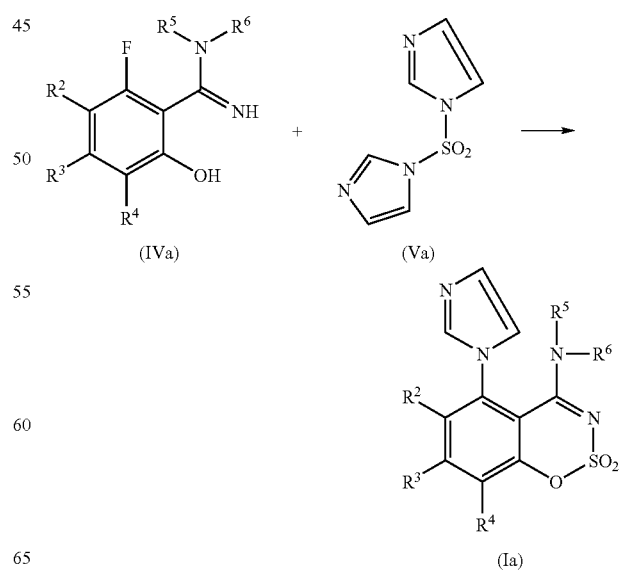

In a fourth embodiment (D) of the present invention, the compounds of the general formula (I) are prepared by reacting 4-amino-1,2,3-benzoxathiazine derivatives of the general formula (Ib) in which $R^1$, $R^2$, $R^3$, $R^4$ are each as defined above with alkylating agents, acylating agents or sulphonating agents of the general formula (VI) and/or (VII) to give compounds of the general formula (Ic) and/or (I), where $R^1$, $R^2$, $R^3$, $R^4$, $R^5$ and $R^6$ are each as defined above and Z is a leaving group, for example halide, sulphonate, thiocarboxylate, carboxylate:

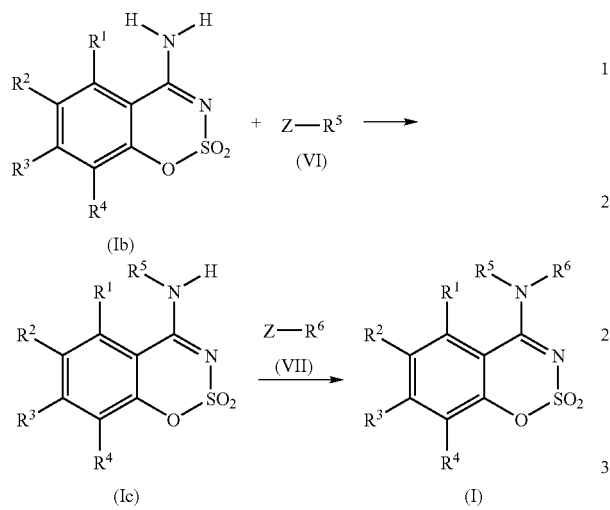

Useful alkylating agents include all customary reagents, for example alkyl halides, alkenyl halides, alkynyl halides, benzyl halides, or the sulphonic esters thereof. Examples include methyl iodide, allyl bromide, propargyl bromide, benzyl bromide, dimethyl sulphate, methyl trifluoromethanesulphonate.

Useful acylating agents include all customary reagents, for example (thio)carbonyl halides, or (thio)carboxylic anhydrides. Examples include acetyl chloride, cyclopropyl chloride, dimethylcarbamoyl chloride, ethyl chloroformate, methyl chlorothioformate, nicotinyl chloride, trifluoroacetic anhydride. Useful sulphonylating reagents include sulphonyl halides and sulphonyl anhydrides. Examples include trifluoromethanesulphonic anhydride, methanesulphonyl chloride, para-toluenesulphonyl chloride.

In the case that $R^6$ is a monosubstituted amino(thio)carbonyl radical, in a fifth embodiment (E) of the present invention, the compounds of the general formula (I) are prepared by reacting 4-amino-1,2,3-benzoxathiazine derivatives of the general formula (Ib) or (Ic), in which $R^1$, $R^2$, $R^3$, $R^4$, $R^5$, $R^7$, X are each as defined above, with iso(thio)cyanates of the general formula (VIII):

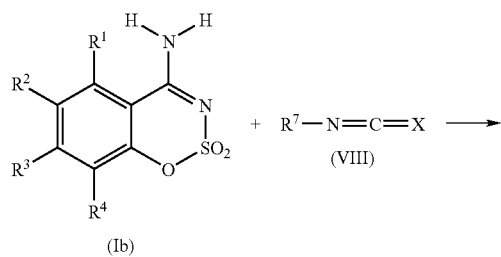

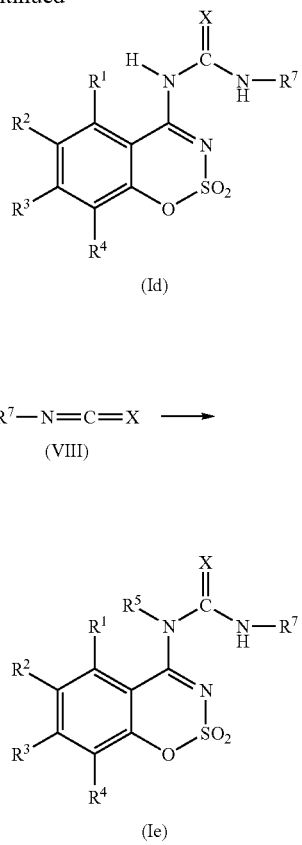

In the aforementioned process variants, inert solvents are used in each case. In the third embodiment, (C), it is also possible to work without solvent. Inert solvents are understood in the context of the present invention to mean solvents which are inert under the particular reaction conditions, i.e., more particularly, do not react with the reactants, but need not be inert under all reaction conditions.

Examples of organic solvents which can be used in the context of the present invention are aromatic or aliphatic solvents, such as benzene, toluene, xylene, mesitylene, hexane, heptane, octane, cyclohexane; aliphatic and aromatic halohydrocarbons, such as methylene chloride, dichlorethane, chloroform, carbon tetrachloride, chlorobenzene, dichlorobenzene, ethers, such as diethyl ether, dibutyl ether, diisobutyl ether, methyl tert-butyl ether, isopropyl ethyl ether, diisopropyl ether, tetrahydrofuran and dioxane; additionally also dimethyl sulphoxide, and acid amide derivatives, such as N,N-dimethylformamide, N,N-dimethylacetamide and N-methyl-2-pyrrolidone, and also carboxylic esters, such as ethyl acetate, or else diglyme, dimethylglycol; nitriles such as acetonitrile, propionitrile or butyronitrile, and ketones such as acetone, methyl ethyl ketone or cyclohexanone. Particular preference is given to toluene, xylene, dichlorobenzene, chlorobenzene, acetonitrile, acetone, butyronitrile or ethyl acetate. However, the present invention is not restricted to the solvents specified above by way of example.

The reaction temperature at which the reactions in the above embodiments can be performed may vary within wide ranges. Corresponding temperatures are specified in the particular embodiments of the reactions. Furthermore, the reactions can be performed at a temperature of 0 to 160° C., preferably 20 to 120° C.

The reactions of the present invention are generally performed under standard pressure. However, it is also possible to work under elevated pressure or reduced pressure—generally between 0.1 bar and 10 bar.

The processes for preparing the inventive 4-amino-1,2,3-benzoxathiazine derivatives of the general formula (I) are optionally performed in the presence of a basic or acidic reaction auxiliary or cleaving reagent.

Useful such substances include all customary inorganic or organic bases. These include, for example, alkali metal or alkaline earth metal hydrides, hydroxides, amides, alkoxides, acetates, carbonates or hydrogencarbonates, for example lithium, sodium, potassium or calcium hydride, lithium, sodium or potassium amide, sodium or potassium methoxide, sodium or potassium ethoxide, sodium or potassium propoxide, aluminium isopropoxide, sodium or potassium tert-butoxide, sodium or potassium hydroxide, ammonium hydroxide, sodium, potassium or calcium acetate, ammonium acetate, sodium, potassium or calcium carbonate, ammonium carbonate, sodium or potassium hydrogencarbonate, and also basic organic nitrogen compounds, such as trimethylamine, triethylamine, tripropylamine, tributylamine, ethyl-diisopropyl amine, N,N-dimethylcyclohexylamine, dicyclohexylamine, ethyldicyclohexylamine, N,N-dimethylaniline, N,N-dimethylbenzylamine, pyridine, 2-methyl-, 3-methyl- and 4-methylpyridine, 2,4-dimethyl-, 2,6-dimethyl-, 3,4-dimethyl- and 3,5-dimethylpyridine, 5-ethyl-2-methylpyridine, N-methylpyridine, 4-(N,N-dimethylamino)pyridine, diazabicyclooctane (DABCO), diazabicyclononene (DBN) or diazabicycloundecene (DBU).

Useful acidic reaction auxiliaries include all customary inorganic or organic acids. These include, for example, mineral acids such as sulphuric acid $H_2SO_4$, phosphoric acid $H_3PO_4$ or hydrochloric acid HCl, or organic acids such as formic acid, acetic acid or trifluoroacetic acid.

Coupled with good plant compatibility, favorable homeotherm toxicity and good environmental compatibility, the inventive active ingredients are suitable for protection of plants and plant organs, for increasing yields, improving the quality of the yield and for controlling animal pests, especially insects, arachnids, helminths, nematodes and molluscs, which occur in agriculture, in gardening, in animal breeding, in forests, in gardens and leisure facilities, in stock and material protection, and in the hygiene sector. They can preferably be used as crop protection compositions. They are effective against normally sensitive and resistant species, and against all or individual stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is additionally possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus,*

*Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber*.

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips Havens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The efficacy of the compounds of the formula (I) can be enhanced by adding ammonium salts and phosphonium salts. The ammonium salts and phosphonium salts are defined by formula (IX)

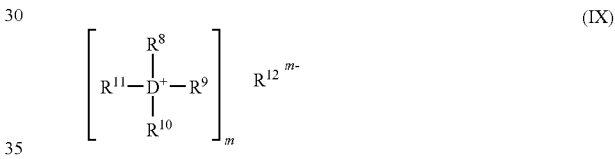

in which

D is nitrogen or phosphorus,

D is preferably nitrogen, $R^8$, $R^9$, $R^{10}$ and $R^{11}$ are each independently hydrogen or in each case optionally substituted $C_1$-$C_8$-alkyl or mono- or polyunsaturated, optionally substituted $C_1$-$C_8$-alkylene, where the substituents may be selected from halogen, nitro and cyano, $R^8$, $R^9$, $R^{10}$ and $R^{11}$ are preferably each independently hydrogen or in each case optionally substituted $C_1$-$C_4$-alkyl, where the substituents may be selected from halogen, nitro and cyano, $R^8$, $R^9$, $R^{10}$ and $R^{11}$ are more preferably each independently hydrogen, methyl, ethyl, n-propyl, isopropyl, n-butyl, isobutyl, s-butyl or t-butyl, $R^8$, $R^9$, $R^{10}$ and $R^{11}$ even more preferably represent hydrogen, m is 1, 2, 3 or 4, m is preferably 1 or 2, $R^{12}$ is an inorganic or organic anion, $R^{12}$ is preferably bicarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate, citrate or oxalate, $R^{12}$ is more preferably lactate, sulphate, monohydrogenphosphate, dihydrogenphosphate, nitrate, thiosulphate, thiocyanate, citrate, oxalate or formate, $R^{12}$ is most preferably sulphate.

The ammonium salts and phosphonium salts of the formula (IX) can be used in a wide concentration range to enhance the action of crop protection compositions comprising compounds of the formula (I). In general, the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active ingredient concentration. The concentration of the salt in the formulation is typically 1-50% by weight.

In one preferred embodiment of the invention, not just an ammonium salt and/or phosphonium salt but also a penetrant is added to the crop protection compositions to enhance the activity. An enhancement of activity can be observed even in these cases. The present invention thus also provides for the use of penetrants, and also for the use of a combination of penetrant and ammonium salts and/or phosphonium salts for increasing the activity of crop protection compositions which comprise acaricidally/insecticidally active compounds of the formula (I) as active ingredient. Finally, the invention also provides the use of these compositions for controlling harmful insects.

Useful penetrants in the present context are all those substances which are usually used for improving the penetration of agrochemical active ingredients into plants. Penetrants are defined in this context by their ability to penetrate from the aqueous spray liquor and/or from the spray coating into the cuticle of the plant and thereby increase the mobility of active ingredients in the cuticle. The method described in the literature (Baur et al., 1997, *Pesticide Science* 51, 131-152) can be used to determine this property.

Suitable penetrants are, for example, alkanol alkoxylates. Inventive penetrants are alkanol alkoxylates of the formula R—O—(-AO)$_v$—R'  (X)

in which
R is straight-chain or branched alkyl having 4 to 20 carbon atoms,
R' is hydrogen, methyl, ethyl, n-propyl, i-propyl, n-butyl, i-butyl, t-butyl, n-pentyl or n-hexyl,
AO is an ethylene oxide radical, a propylene oxide radical, a butylene oxide radical or mixtures of ethylene oxide and propylene oxide radicals or butylene oxide radicals and
v is from 2 to 30.

A preferred group of penetrants is that of alkanol alkoxylates of the formula

R—O—(-EO—)$_n$—R'  (X-a)

in which
R is as defined above,
R' is as defined above,
EO is —CH$_2$—CH$_2$—O— and
n is from 2 to 20.

A further preferred group of penetrants is that of alkanol alkoxylates of the formula R—O—(-EO—)$_p$—(—PO—)$_q$—R'  (X-b)

in which
R is as defined above,
R' is as defined above,
EO is —CH$_2$—CH$_2$—O—,
PO is

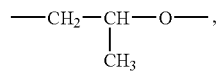

p is from 1 to 10 and
q is from 1 to 10.

A further preferred group of penetrants is that of alkanol alkoxylates of the formula R—O—(—PO—)$_r$-(EO—)$_s$—R'  (X-c)

in which
R is as defined above,
R' is as defined above,
EO is —CH$_2$—CH$_2$—O—,
PO is

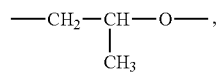

r is from 1 to 10 and
s is from 1 to 10.

A further preferred group of penetrants is that of alkanol alkoxylates of the formula R—O—(-EO—)$_p$—(—BO—)$_q$—R'  (X-d)

in which
R and R' have the meanings given above,
EO is —CH$_2$—CH$_2$—O—,
BO is

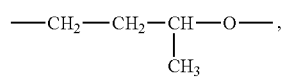

p is from 1 to 10 and
q is from 1 to 10.

A further preferred group of penetrants is that of alkanol alkoxylates of the formula R—O—(—BO—)$_r$—(-EO—)$_s$—R'  (X-e)

in which
R and R' have the meanings given above,
BO is

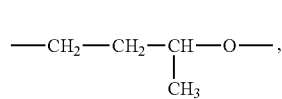

EO is CH$_2$—CH$_2$—O—,
r is from 1 to 10 and
s is from 1 to 10.

A further preferred group of penetrants is that of alkanol alkoxylates of the formula CH$_3$—(CH$_2$)$_t$—CH$_2$—O—(—CH$_2$—CH$_2$—O—)$_u$—R'  (X-f)

in which
R' is as defined above,
t is from 8 to 13,
u is from 6 to 17.

In the formulae given above,

R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

One example of an alkanol alkoxylate of the formula (X-c) is 2-ethylhexyl alkoxylate of the formula

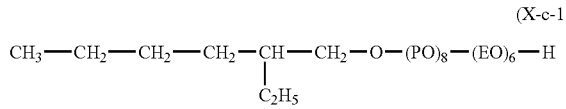

(X-c-1)

in which
EO is —$CH_2$—$CH_2$—O—,
PO is

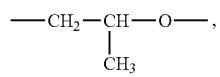

and
the numbers 8 and 6 represent average values.

One example of an alkanol alkoxylate of the formula (X-d) is that of the formula

(X-d-1)

in which
EO is $CH_2$—$CH_2$—O—,
BO is

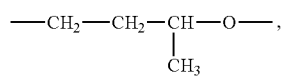

and
the numbers 10, 6 and 2 represent average values.

Particularly preferred alkanol alkoxylates of the formula (X-f) are compounds of this formula in which
t is from 9 to 12 and
u is from 7 to 9.

A very particularly preferred example is alkanol alkoxylate of the formula (X-f-1)

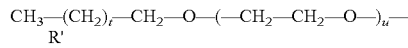

(X-f-1)

in which
t is the average value 10.5 and
u is the average value 8.4.

The alkanol alkoxylates are defined in general terms by the above formulae. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865).

Suitable penetrants also include, for example, substances which promote the solubility of the compounds of the formula (I) in the spray coating. These include, for example, mineral and vegetable oils. Suitable oils are all mineral or vegetable oils—modified or otherwise—which can usually be used in agrochemical compositions. Examples include sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters.

The concentration of penetrant can be varied within a wide range. In the case of a formulated crop protection composition, it is generally 1 to 95% by weight, preferably 1 to 55% by weight, more preferably 15-40% by weight. In the ready-to-use compositions (spray liquors), the concentration is generally between 0.1 and 10 g/l, preferably between 0.5 and 5 g/l.

Combinations of active ingredient, salt and penetrant emphasized in accordance with the invention are listed in the table below. Here, "according to test" means that any compound which acts as a penetrant in the cuticle penetration test (Baur et al., 1997, *Pesticide Science* 51, 131-152) is suitable:

| # | Active ingredient | Salt | Penetrant |
|---|---|---|---|
| 1 | I | ammonium sulphate | according to test |
| 2 | I | ammonium lactate | according to test |
| 3 | I | ammonium nitrate | according to test |
| 4 | I | ammonium thiosulphate | according to test |
| 5 | I | ammonium thiocyanate | according to test |
| 6 | I | ammonium citrate | according to test |
| 7 | I | ammonium oxalate | according to test |
| 8 | I | ammonium formate | according to test |
| 9 | I | ammonium hydrogenphosphate | according to test |
| 10 | I | ammonium dihydrogenphosphate | according to test |
| 11 | I | ammonium carbonate | according to test |
| 12 | I | ammonium benzoate | according to test |
| 13 | I | ammonium sulphite | according to test |
| 14 | I | ammonium benzoate | according to test |
| 15 | I | ammonium hydrogenoxalate | according to test |
| 16 | I | ammonium hydrogencitrate | according to test |
| 17 | I | ammonium acetate | according to test |
| 18 | I | tetramethylammonium sulphate | according to test |
| 19 | I | tetramethylammonium lactate | according to test |
| 20 | I | tetramethylammonium nitrate | according to test |
| 21 | I | tetramethylammonium thiosulphate | according to test |
| 22 | I | tetramethylammonium thiocyanate | according to test |
| 23 | I | tetramethylammonium citrate | according to test |
| 24 | I | tetramethylammonium oxalate | according to test |
| 25 | I | tetramethylammonium formate | according to test |
| 26 | I | tetramethylammonium hydrogenphosphate | according to test |
| 27 | I | tetramethylammonium dihydrogenphosphate | according to test |
| 28 | I | tetraethylammonium sulphate | according to test |
| 29 | I | tetraethylammonium lactate | according to test |
| 30 | I | tetraethylammonium nitrate | according to test |
| 31 | I | tetraethylammonium thiosulphate | according to test |
| 32 | I | tetraethylammonium thiocyanate | according to test |
| 33 | I | tetraethylammonium citrate | according to test |
| 34 | I | tetraethylammonium oxalate | according to test |
| 35 | I | tetraethylammonium formate | according to test |
| 36 | I | tetraethylammonium hydrogenphosphate | according to test |
| 37 | I | tetraethylammonium dihydrogenphosphate | according to test |

If appropriate, the compounds of formula (I) can, at certain concentrations or application rates, also be used as herbicides, safeners, growth regulators or compositions to improve plant properties, or as microbicides, for example as fungicides, antimycotics, bactericides, viricides (including compositions against viroids) or as compositions against MLO (Mycoplasma-like organisms) and RLO (Rickettsia-like organisms). If appropriate, they can also be used as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers and also microencapsulations in polymeric substances.

These formulations are prepared in a known manner, for example by mixing the active ingredients with extenders, that is, liquid solvents, and/or solid carriers, optionally with the use of surfactants, that is to say emulsifiers and/or dispersants, and/or foam-formers. The formulations are prepared either in suitable plants or else before or during application.

The substances used as auxiliaries are substances which are suitable for imparting particular properties to the composition itself and/or to preparations derived therefrom (for example spray liquors, seed dressings), such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat and/or POP-POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO ether adducts; further, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other compostions which improve chemical and/or physical stability may also be present.

The formulations generally comprise between 0.01 and 98% by weight of active ingredient, preferably between 0.5 and 90%.

The active ingredient may be present in its commercially available formulations and in the use fauns, prepared from these formulations, as a mixture with other active ingredients, such as insecticides, attractants, sterilizing agents, bactericides, acaricides, nematicides, fungicides, growth-regulating substances, herbicides, safeners, fertilizers, semiochemicals, or else with compositions for improving the plant properties.

When used as insecticides, the inventive active ingredients may additionally be present in their commercially available formulations and in the use forms, prepared from these formulations, as a mixture with synergistic agents. Synergistic agents are compounds which increase the action of the active ingredients, without it being necessary for the synergistic agent added to be active itself.

When used as insecticides, the inventive active ingredients may additionally be present in their commercially available formulations and in the use forms, prepared from these formulations, as a mixture with inhibitors which reduce degradation of the active ingredient after use in the environment of the plant, on the surface of plant parts or in plant tissues.

The active ingredient content of the use forms prepared from the commercially available formulations can vary within wide limits. The active ingredient concentration of the use forms can be from 0.00000001 to 95% by weight of active ingredient, preferably between 0.00001 and 1% by weight.

The compounds are employed in a customary manner appropriate for the use forms.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood to mean all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example cuttings, tubers, rhizomes, offshoots and seeds.

The inventive treatment of the plants and plant parts with the active ingredients is carried out directly or by allowing the compounds to act on the surroundings, environment or storage space by the customary treatment methods, for example by immersion, spraying, evaporation, fogging, scattering, painting on, injecting, pouring on, and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are in each case commercially available or in use are treated according to the invention. Plant cultivars are to be understood to mean plants having new properties ("traits") and which have been obtained by conventional breeding, by mutagenesis or by recombinant DNA techniques. They can be cultivars, bio- or genotypes.

Depending on the plant species or plant cultivars, their location and growth conditions (soils, climate, vegetation period, diet), the treatment according to the invention may also result in superadditive ("synergistic") effects. Thus possible are, for example, reduced application rates and/or a widening of the activity spectrum and/or an increase of the activity of the compounds and compositions usable in accordance with the invention, better plant growth, increased tolerance to high or low temperatures, increased tolerance to drought or to water or soil salt content, increased flowering performance, easier harvesting, accelerated maturation, higher harvest yields, higher quality and/or higher nutrient value of the harvested products, increased storability and/or processability of the harvested products, which exceed the effects normally to be expected.

The transgenic plants or plant cultivars (i.e. those obtained by genetic engineering) which are preferably treated according to the invention include all plants which, in the genetic modification, received genetic material which imparted particular advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugarbeet, tomatoes, peas and other types of vegetable, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are additionally particularly emphasized are the increased tolerance of the plants to certain herbicidally active ingredients, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya bean), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants stated can be treated particularly advantageously in accordance with the invention with the compounds of the general formula I or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The inventive active ingredients act not only against plant, hygiene and stored product pests, but also in the veterinary sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Hae-* matopota spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Deunanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredients of the formula (I) are also suitable for controlling arthropods which infest agricultural productive livestock, for example cattle, sheep, goats, horses, pigs, donkeys, camels, buffalo, rabbits, chickens, turkeys, ducks, geese and bees, other pets, for example dogs, cats, caged birds and aquarium fish, and also so-called test animals, for example hamsters, guinea pigs, rats and mice. By controlling these arthropods, cases of death and reduction in productivity (for meat, milk, wool, hides, eggs, honey etc.) should be diminished, so that more economic and easier animal husbandry is possible by the use of the inventive active ingredients.

The inventive active ingredients are used in the veterinary sector and in animal husbandry in a known manner by enteral administration in the form of, for example, tablets, capsules, potions, drenches, granules, pastes, boluses, the feed-through process and suppositories, by parenteral administration, for example by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100 to 10 000-fold dilution, or they may be used as a chemical bath.

It has additionally been found that the inventive compounds also have a strong insecticidal action against insects which destroy industrial materials.

The following insects may be mentioned as examples and as preferred—but without limitation:
beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec., Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood to mean non-living materials, such as, preferably, plastics, adhesives, sizes, papers and cards, leather, wood and processed wood products and coating compositions.

The ready-to-use compositions can also comprise other insecticides, if appropriate, and also one or more fungicides, if appropriate.

The inventive compounds can additionally be employed for protecting objects which come into contact with saltwater or brackish water, such as hulls, screens, nets, buildings, moorings and signalling systems, against fouling.

Furthermore, the inventive compounds can be used alone or in combinations with other active ingredients as antifouling compositions.

The active ingredients are also suitable for controlling animal pests in the domestic field, in hygiene and in the protection of stored products, in particular insects, arachnids and mites, which are found in enclosed spaces, for example dwellings, factory halls, offices, vehicle cabins and the like. They can be employed alone or in combination with other active ingredients and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Avicularidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais*, *Stegobium paniceum*.

From the order of the Diptera, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga carnaria*, *Simulium* spp., *Stomoxys calcitrans*, *Tipula paludosa*.

From the order of the Lepidoptera, for example, *Achroia grisella*, *Galleria mellonella*, *Plodia interpunctella*, *Tinea cloacella*, *Tinea pellionella*, *Tineola bisselliella*.

From the order of the Siphonaptera, for example, *Ctenocephalides canis*, *Ctenocephalides felis*, *Pulex irritans*, *Tunga penetrans*, *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp., *Tetramorium caespitum*.

From the order of the Anoplura, for example, *Pediculus humanus capitis*, *Pediculus humanus corporis*, *Pemphigus* spp., *Phylloera vastatrix*, *Phthirus pubis*.

From the order of the Heteroptera, for example, *Cimex hemipterus*, *Cimex lectularius*, *Rhodinus prolixus*, *Triatoma infestans*.

In the household insecticides sector, they are used alone or in combination with other suitable active ingredients, such as phosphoric acid esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Illustration of the Processes and Intermediates

The preparation and use examples which follow illustrate the invention, without restricting it.

When, for example, 2-cyanophenyl sulphamate is used as the starting material, the course of the process according to the invention in the first embodiment can be illustrated by the following formula scheme:

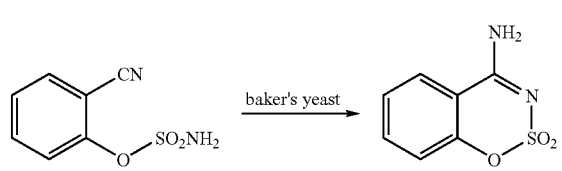

When, for example, 5-fluoro-2-hydroxybenzonitrile is used as the starting material, the course of the process according to the invention in the second embodiment can be illustrated by the following formula scheme:

Some 2-cyanophenols are known and can be prepared by processes known per se (cf. US 2006/0052374, WO 1997/037967, WO 2007/089646).

When, for example, 2-chloro-6-hydroxybenzenecarboximidamide and sulphonylbisimidazole are used as starting materials, the course of the process according to the invention in the third embodiment can be illustrated by the following formula scheme:

When, for example, 4-amino-5,7-dibromo-1,2,3-benzoxathiazine 2,2-dioxide and methyl trifluoromethanesulphonate are used as starting materials, the course of the process according to the invention in the fourth embodiment can be illustrated by the following formula scheme:

or, when, for example, 5,7-dibromo-4-methylamino-1,2,3-benzoxathiazine 2,2-dioxide and trifluoroacetic anhydride are used as starting materials, the course of the process according to the invention in the fourth embodiment can also be illustrated by the following formula scheme:

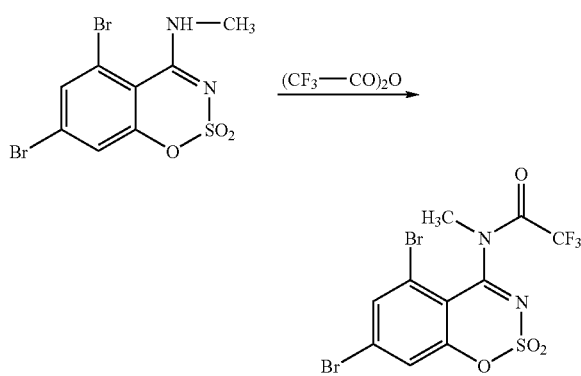

When, for example, 4-amino-5-fluoro-1,2,3-benzoxathiazine 2,2-dioxide and cyclohexyl isocyanate are used as starting materials, the course of the process according to the invention in the fifth embodiment can be illustrated by the following formula scheme:

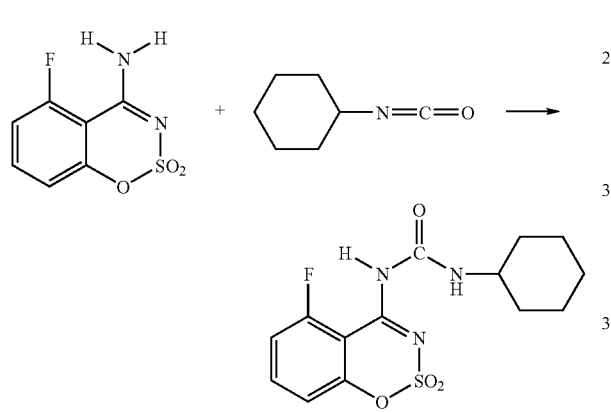

or, when, for example, 5-difluoromethoxy-4-methylamino-1,2,3-benzoxathiazine 2,2-dioxide and methyl isothiocyanate are used as starting materials, the course of the process according to the invention in the fifth embodiment can also be illustrated by the following formula scheme:

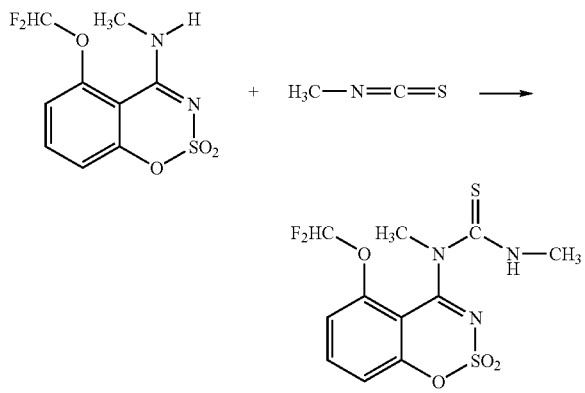

Preparation of the Amidinophenols of the Formula (IV)

Some amidinophenols of the general formula (IV) are commercially available or can be prepared by known methods [cf. EP626372, WO 1997/49404, WO 2003/047517, U.S. Pat. No. 5,863,929, Journal of Medicinal Chemistry (2001), 44(21), 3424-3439), Bulletin de la Societe Chimique de France (1958), 185-187].

For example, proceeding from 2-fluorobenzonitriles of the general formula (XI) in which $R^1$, $R^2$, $R^3$ and $R^4$ are each as defined above, by reaction with acetohydroxamic acid in the presence of potassium tert-butoxide, the 3-amino-1,2-benzisoxazoles of the general formula (XII) are obtained [cf. Chem. Ber. 100 (10), (1967), 3326-3330 and J. of Heterocyclic Chem. (1989), 26(5), 1293-1298 and Tetrahedron Lett. (1996), 37 (17), 2885-2886 and J. Med. Chem. (2003), 46, 4405-4418 and EP353631], which can subsequently be converted by reaction with orthocarboxylic esters and sodium borohydride to the N-alkyl-3-amino-1,2-benzisoxazoles or N-aralkyl-3-amino-1,2-benzisoxazoles of the general formula (XIIa) [cf. Synthesis (1980) 743 and Arch. Pharmazie (Weinheim) 322 (1989), 583-587].

The 3-amino-1,2-benzisoxazoles of the general formulae (XII) and (XIIa) can subsequently be cleaved reductively to the amidinophenols of the general formulae (IVb) and (IVc):

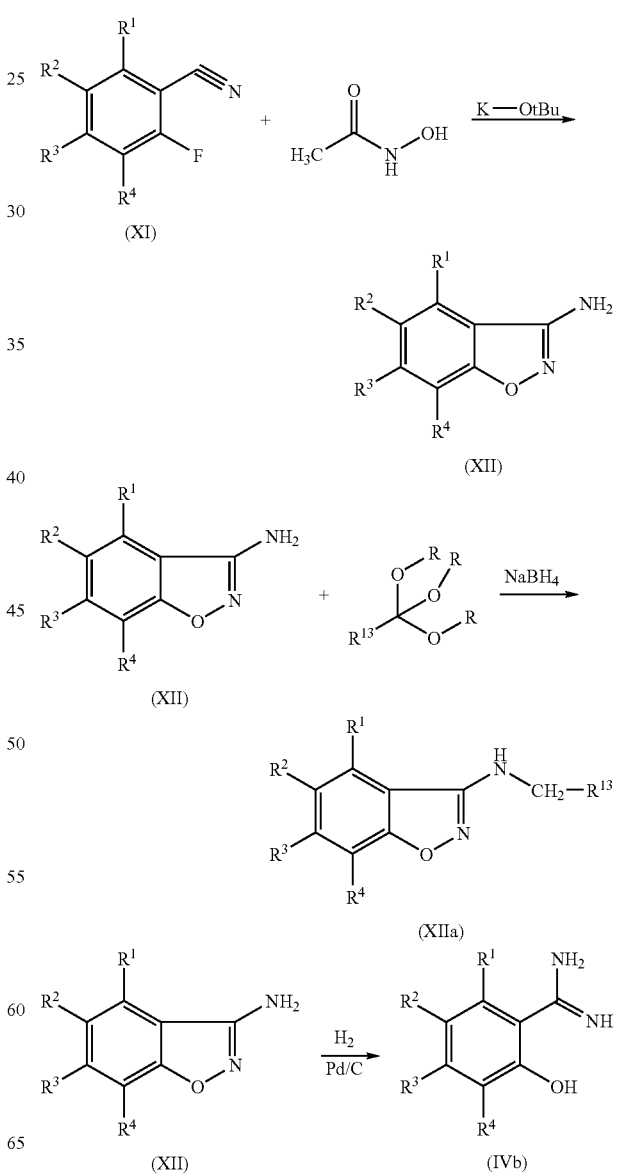

-continued

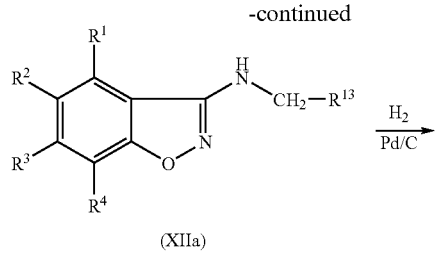

(XIIa)

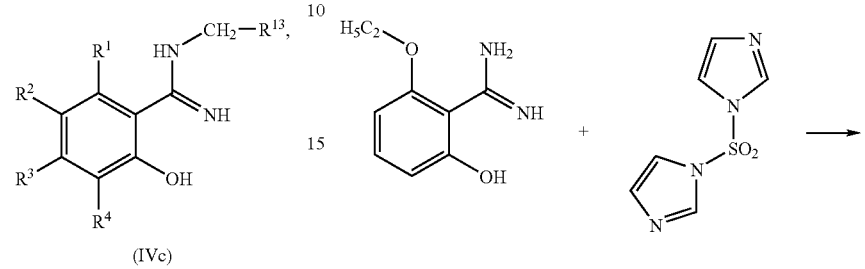

(IVc)

where $R^{13}$ is hydrogen, $C_1$-$C_6$-alkyl, aryl, preferably and more preferably hydrogen, $C_1$-$C_4$-alkyl, phenyl.

PREPARATION EXAMPLES

Preparation of
4-amino-5-fluoro-1,2,3-benzoxathiazine 2,2-dioxide
(I-1)

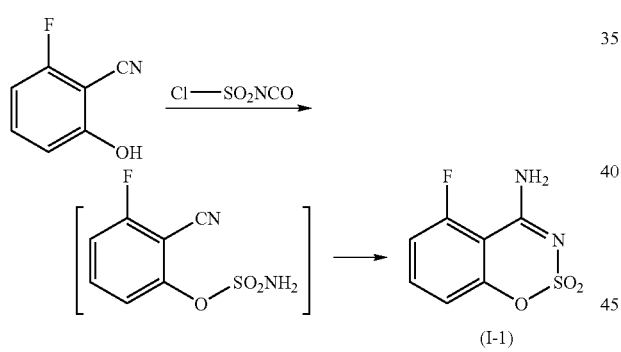

8.0 g (58.3 mmol) of 2-cyano-3-fluorophenol are dissolved in 100 ml of anhydrous toluene. With exclusion of moisture and under protective argon gas, a solution of 8.489 g (60 mmol) of chlorosulphonyl isocyanate is added dropwise, in the course of which slight exothermicity occurs. The mixture is stirred at 50° C. for 16 hours; phenol is no longer detectable by thin-layer chromatography. The mixture is heated under reflux for 16 hours; no further evolution of HCl gas takes place. The mixture is concentrated under reduced pressure, taken up in acetonitrile and admixed with aqueous acetonitrile. After stirring at room temperature for 1 hour, the mixture is concentrated, and the residue is dissolved in dichloromethane and washed with water. After drying and concentrating the organic phase, 13 g of a reaction mixture are obtained, which is chromatographed on silica gel (450 g, 40-63 μm) with dichloromethane/methanol=99/1. 1.3 g of a fraction are isolated, which consists of two components at log P=0.76 and 1.06. After separating this mixture by means of HPLC, 0.8 g of 4-amino-5-fluoro-1,2,3-benzoxathiazine 2,2-dioxide is obtained as a white solid.

Preparation of
4-amino-5-ethoxy-1,2,3-benzoxathiazine 2,2-dioxide
(I-2)

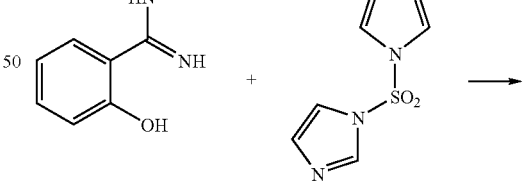

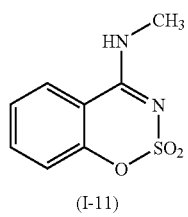

(I-2)

0.25 g (1.39 mmol) of 2-ethoxy-6-hydroxybenzenecarboximidamide is stirred without solvent with 0.65 g (3.28 mmol) of 1,1'-sulphonyldiimidazole at 130° C. for 18 hours. Cooling is followed by stirring the mixture with water and removing with dichloromethane. The organic phase is dried over magnesium sulphate and concentrated under reduced pressure. This gives 0.2 g of a pale yellow, crystalline material.

Preparation of
N-methyl-4-amino-1,2,3-benzoxathiazine
2,2-dioxide (I-11)

0.18 g (1.20 mmol) of 2-hydroxyl-N-methylbenzenecarboximidamide is stirred with 0.48 g (2.42 mmol) of 1,1'-sulphonyldiimidazole at 120° C. for 18 hours. Cooling is followed by stirring the mixture with water and then decanting off from the water. The remaining residue is chromatographed on silica gel (450 g, 40-63 μm) with dichloromethane/methanol=99/1. 87 mg of product are isolated.

Preparation of 1-cyclohexyl-3-(5-ethoxy-2,2-dioxido-1,2,3-benzoxathiazin-4-yl)urea

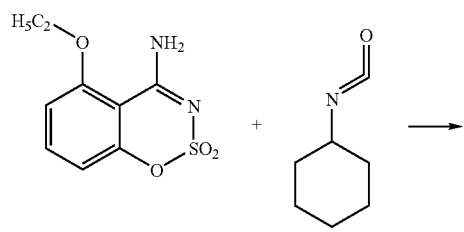

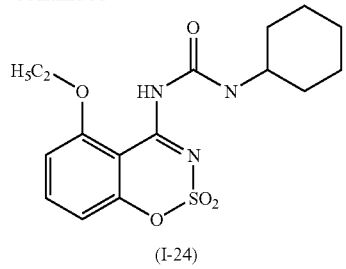

(I-24)

0.15 g (0.61 mmol) of 4-amino-5-ethoxy-1,2,3-benzoxathiazine 2,2-dioxide is stirred with 0.1 g (0.79 mmol) of cyclohexyl isocyanate in 30 ml of dry tetrahydrofuran in the presence of 10 mg of DBU, first at room temperature for 1 hour and then at 40° C. for 18 hours. The mixture is concentrated under reduced pressure, and the residue is dissolved in dichloromethane and washed with water. The organic phase is dried over magnesium sulphate and concentrated under reduced pressure. This gives 0.15 g of crude product which, after dissolution in 14 ml of acetonitrile and 6 ml of water, is purified by means of reversed phase HPLC (Kromasil 100 C18, 250×40 mm, 5 μm, 0.01% HCOOH/H2O acetonitrile gradient 34/66, isocratic). This gives 55 mg (24.2% of theory) of compound I-24 as a white solid.

The compounds of the general formula (I) described in the table which follows are obtained according to or analogously to the above-described synthesis examples:

TABLE 1 compounds of the formula (I)

(I)

| No. | Phys. data | $R^1$ | $R^2$ | $R^3$ | $R^4$ | $R^5$ | $R^6$ |
|---|---|---|---|---|---|---|---|
| I-1 | 1H NMR 13C NMR | F | H | H | H | H | H |
| I-2 | 1H NMR 13C NMR | $OCH_2CH_3$ | H | H | H | H | H |
| I-3 | 1H NMR 13C NMR | $OCH_3$ | H | H | H | H | H |
| I-4 | 1H NMR 13C NMR | $CH_3$ | H | H | H | H | H |
| I-5 | 1H NMR 13C NMR | Cl | H | H | H | H | H |
| I-6 | 1H NMR 13C NMR | Br | H | H | $OCH_3$ | H | H |
| I-7 | 1H NMR 13C NMR | H | H | Cl | CN | H | H |
| I-8 | 1H NMR 13C NMR | H | H | H | $OCH_3$ | H | H |
| I-9 | 1H NMR 13C NMR | H | H | F | H | H | H |
| I-10 | 1H NMR 13C NMR | H | F | H | H | H | H |
| I-11 | 1H NMR 13C NMR | H | H | H | H | $CH_3$ | H |
| I-12 | 1H NMR | $OCHF_2$ | H | H | H | H | H |
| I-13 | 1H NMR | $CF_3$ | H | H | H | H | H |

TABLE 1-continued compounds of the formula (I)

(I)

| No. | Phys. data | R¹ | R² | R³ | R⁴ | R⁵ | R⁶ |
|---|---|---|---|---|---|---|---|
| I-14 | 1H NMR | N-pyrrole (N-linked) | H | H | H | H | H |
| I-15 | 1H NMR | OCH₂CH₃ | H | H | H | CH₃ | H |
| I-16 | | OCHF₂ | H | H | H | CH₃ | H |
| I-17 | | OCHF₂ | H | H | H | CH₃ | CH₃ |
| I-18 | | OCHF₂ | H | H | H | CO—CH₃ | H |
| I-19 | | OCHF₂ | H | H | H | CO—CF₃ | H |
| I-20 | | OCHF₂ | H | H | H | CO—OCH₃ | H |
| I-21 | | OCHF₂ | H | H | H | CO—OC₂H₅ | H |
| I-22 | 1H NMR | CF₃ | H | H | H | CH₃ | H |
| I-23 | 1H NMR | OC₂H₅ | H | H | H | CO—NH—CH(CH₃)₂ | H |
| I-24 | 1H NMR | OC₂H₅ | H | H | H | CO—NH-cyclohexyl | H |

1H NMR data (600 MHz, solvent: CD3CN or [D6]-DMSO, internal standard: tetramethylsilane δ=0.00 ppm; s=singlet, br. s=broad singlet, d=doublet, dd=double doublet, dt=doublet of a triplet; m=multiplet, q=quartet, t=triplet)

13C NMR data (150.9 MHz, solvent: CD3CN or [D6]-DMSO, internal standard: tetramethylsilane δ=0.00 ppm)

I-1:
¹H NMR: δ ([D6]-DMSO)=7.26 (d, 1H); 7.30-7.35 (m, 1H); 7.80 (m, 1H); 8.30 (br. s, 1H); 9.13 (br. s, 1H) ppm
¹³C NMR: δ ([D6]-DMSO)=102.5; 113.5; 115.7; 137.2; 154.0; 159.1; 159.5 ppm I-2:
¹H NMR: δ ([D6]-DMSO)=1.43 (t, 3H); 4.30-4.35 (q, 2H); 6.90-6.93 (m, 1H); 7.08-7.11 (m, 1H); 7.64-7.69 (m, 1H); 8.25 (br. s, 1H); 8.97 (br. s, 1H) ppm
¹³C NMR: δ ([D6]-DMSO)=14.2; 65.9; 101.7; 109.7; 111.0; 136.4; 154.6; 157.7; 161.3 ppm I-3:
¹H NMR: δ (CD3CN)=4.01 (s, 3H); 6.90 (d, 1H); 7.03 (d, 1H); 7.14 (br. s, 1H); 7.66 (t, 1H); 8.21 (br. s, 1H) ppm
¹³C NMR: δ (CD3CN)=57.9; 102.4; 109.6; 112.2; 137.3; 156.1; 159.8; 162.7 ppm I-4:
¹H NMR: δ ([D6]-DMSO)=2.66 (s, 3H); 7.23 (d, 1H); 7.29 (d, 1H); 7.60 (t, 1H); 8.00 (br. s, 1H); 9.14 (br. s, 1H) ppm
¹³C NMR: δ ([D6]-DMSO)=21.4; 113.9; 116.8; 129.3; 134.6; 138.5; 153.6; 163.3 ppm I-5:
¹H NMR: δ (CD3CN)=7.32 (d, 1H); 7.45 (br. s, 1H); 7.49 (d, 1H); 7.58 (br. s, 1H); 7.67 (t, 1H) ppm
¹³C NMR: δ (CD3CN)=112.5; 119.7; 129.7; 132.9; 136.7; 156.1; 161.8 ppm I-6:
¹H NMR: δ ([D6]-DMSO)=3.90 (s, 3H); 7.40 (d, 1H); 7.69 (d, 1H); 8.45 (br. s, 1H); 9.54 (br. s, 1H) ppm
¹³C NMR: δ ([D6]-DMSO)=56.8; 109.0; 114.9; 118.6; 131.5; 143.8; 148.7; 161.8 ppm I-7:
¹H NMR: δ ([D6]-DMSO)=7.89 (d, 1H); 8.40 (d, 1H); 9.48, 9.51 (br., 2H) ppm
¹³C NMR: δ ([D6]-DMSO)=104.4; 111.5; 111.6; 126.4; 132.77; 142.82; 155.9; 160.6 ppm I-8:
¹H NMR: δ ([D6]-DMSO)=3.90 (s, 3H); 7.38 (t, 1H); 7.49 (d, 1H); 7.63 (d, 1H); 9.03 (br., 2H) ppm
¹³C NMR: δ ([D6]-DMSO)=56.5; 112.7; 117.4; 118.4; 125.1; 142.8; 148.7; 162.5 ppm I-9:
¹H NMR: δ ([D6]-DMSO)=7.39 (dt, 1H); 7.48 (dd, 1H); 8.19 (dd, 1H); 9.10, 9.12 (br., je 1H) ppm
¹³C NMR: δ ([D6]-DMSO)=107.0; 108.9; 113.4; 129.7; 155.2; 161.6; 166.0 ppm I-10:
¹H NMR: δ ([D6]-DMSO)=7.51 (dd, 1H); 7.71 (dt, 1H); 8.02 (dd, 1H); 9.09 (br. s, 1H); 9.18 (br. s, 1H) ppm
¹³C NMR: δ ([D6]-DMSO)=113.0; 113.3; 121.4; 123.7; 149.7; 158.2; 161.5 ppm I-11:
¹H NMR: δ ([D6]-DMSO)=2.95 (s, 3H); 7.41-7.48 (m, 2H); 7.75-7.78 (m, 1H); 8.04-8.06 (m, 1H); 9.57 (br. s, 1H) ppm
¹³C NMR: δ ([D6]-DMSO)=28.2; 112.4; 118.9; 125.3; 125.9; 135.6; 152.6; 159.7 ppm I-12:
¹H NMR: δ ([D6]-DMSO)=7.20 (m, 1H); 7.25-7.28 (m, 1H); 7.79 (m, 1H); 7.83 (t, 1H); 8.08 (br. s, 1H); 9.16 (br. s, 1H) ppm I-13:
¹H NMR: δ ([D6]-DMSO)=7.74-7.76 (m, 1H); 7.87-7.89 (m, 1H); 7.93-7.95 (m, 1H) ppm
I-14:
¹H NMR: δ ([D6]-DMSO)=7.28-7.30 (m, 1H); 7.48 (m, 1H); 7.65 (d, 1H); 7.95-7.97 (m, 1H); 8.26-8.27 (d, 1H); 8.66 (m, 1H) ppm
I-15:
¹H NMR: δ ([D6]-DMSO)=1.44 (t, 3H); 2.99-3.00 (d, 3H); 4.32-4.37 (q, 2H); 6.91-6.94 (m, 1H); 7.10-7.12 (m, 1H); 7.62-7.67 (m, 1H); 8.81 (br. s, 1H) ppm.
I-22:
¹H NMR: δ ([D₆]-DMSO)=2.98 (s, 3H); 7.74-7.76 (m, 1H); 7.87-7.96 (m, 2H); 8.27 (br. s, 1H) ppm.
I-23:
¹H NMR: δ ([D₆]-DMSO)=1.27-1.28 (d, 6H); 1.46 (t, 3H); 4.16-4.21 (m, 1H); 4.27-4.33 (q, 2H); 6.93-6.95 (m, 1H); 7.09-7.11 (m, 1H); 7.64-7.68 (m, 1H); 8.57 (d, 1H) ppm
I-24:
¹H NMR: δ ([D₆]-DMSO)=1.25-1.85 (m, 10H); 1.46 (t, 3H); 3.64-3.67 (m, 1H); 4.34-4.38 (q, 2H); 7.05-7.07 (m, 1H); 7.19-7.21 (m, 1H); 7.76-7.80 (m, 1H); 8.04-8.05 (d, 1H); 9.98 (s, 1H) ppm.

Preparation of Starting Materials of the Formula (XII)

Example 4

Preparation of 3-amino-4-fluoro-1,2-benzisoxazole

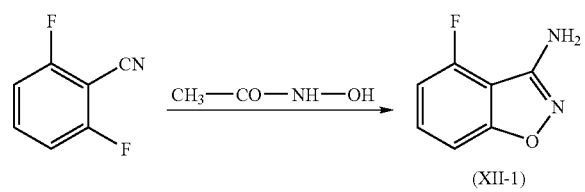

(XII-1)

4.00 g (35.65 mmol) of potassium tert-butoxide and 2.60 g (34.64 mmol) of acetohydroxamic acid are dissolved in 50 ml of dry dimethylformamide and stirred at room temperature for 45 minutes. After the addition of 3.30 g (23.72 mmol) of 2,6-difluorobenzonitrile, the mixture is stirred at 50° C. for 16 hours. The mixture is concentrated under reduced pressure, and the residue is dissolved in dichloromethane and washed with water. After drying and concentration of the organic phase, 3.2 g of a yellow resin are obtained, which, according to ¹H NMR, is about 85% pure.

Example 5

Preparation of 3-amino-4-(difluoromethoxy)-1,2-benzisoxazole

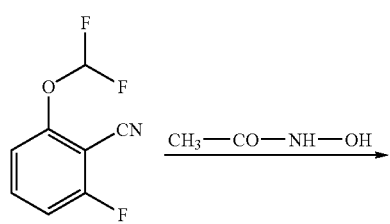

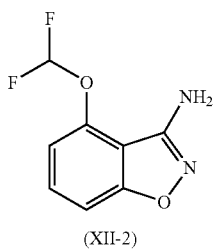

(XII-2)

8.00 g (71.29 mmol) of potassium tert-butoxide and 5.20 g (69.27 mmol) of acetohydroxamic acid are dissolved in 50 ml of dry dimethylformamide and stirred at room temperature for 1 hour. After the addition of 4.40 g (23.51 mmol) of 2-(difluoromethoxy)-6-fluorobenzonitrile, the mixture is stirred first at room temperature for 3 hours and then at 60° C. for 16 hours. The mixture is concentrated under reduced pressure, the residue is stirred with water and the pale olive-coloured precipitate is filtered off with suction. This gives 4.4 g of product, which, according to LC-MS, is about 89% pure.

The compounds of the general formula (XII) described in the table which follows are obtained according to or analogously to the above-described synthesis example:

TABLE 2 compounds of the formula (XII)

(XII)

| No. | Phys. data | $R^1$ | $R^2$ | $R^3$ | $R^4$ |
|---|---|---|---|---|---|
| XII-1 | 1H NMR | F | H | H | H |
| XII-2 | 1H NMR | $OCHF_2$ | H | H | H |
| XII-3 | | Cl | H | H | H |
| XII-4 | | $OCH_3$ | H | H | H |
| XII-5 | | Br | H | H | H |
| XII-6 | | $CF_3$ | H | H | H |
| XII-7 | | $OCF_3$ | H | H | H |
| XII-8 | | $OC_2H_5$ | H | H | H |
| XII-9 | | H | H | H | H |
| XII-10 | | $SCH_3$ | H | H | H |
| XII-11 | | $CH_3$ | H | H | H |
| XII-12 | 1H NMR | 3-chloro-pyridin-2-yloxy | H | H | H |

XII-1:
¹H NMR: δ ([D6]-DMSO)=6.05 (br. s, 2H); 6.97-7.02 (m, 1H); 7.27-7.30 (m, 1H); 7.50-7.55 (m, 1H) ppm
XII-2:
¹H NMR: δ ([D6]-DMSO)=5.82 (br. s, 2H); 6.97-7.00 (m, 1H); 7.27-7.29 (m, 1H); 7.31 (t, 1H); 7.49-7.55 (m, 1H) ppm
XII-12:
¹H NMR: δ ([D₆]-DMSO)=5.25 (br. s, 2H); 6.37-6.41 (m, 1H); 7.21-7.23 (m, 1H); 7.61-7.69 (m, 3H); 7.84-7.87 (m, 1H) ppm.

Preparation of Starting Materials of the Formula (XIIa)

Example 6

Preparation of 4-methoxy-N-methyl-1,2-benzisoxazol-3-amine

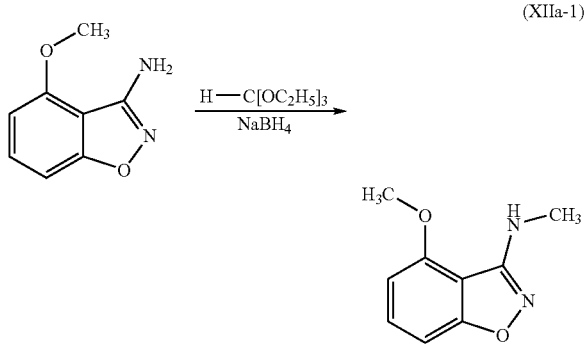
(XIIa-1)

1.8 g [11 mmol] of 3-amino-4-methoxy-1,2-benzisoxazole and 22.5 g [151.8 mmol] of triethyl orthoformate are boiled under reflux with exclusion of moisture for 18 hours. After concentrating by rotary evaporation under reduced pressure, the remaining residue is taken up in 50 ml of ethanol and, after the addition of 3.05 g [80.6 mmol] of sodium borohydride, the mixture is stirred first at room temperature for 3 hours and then at 50° C. for 12 hours. The mixture is concentrated, and the residue is dissolved in dichloromethane and washed with water. After drying and concentrating the organic phase, 1.5 g of the compound (XIIa-1) are obtained as a white solid.

The compounds of the general formula (XIIa) described in the table which follows are obtained according to or analogously to the above-described synthesis example:

TABLE 3 compounds of the formula (XIIa)

(XIIa)

| No. | Phys. data | $R^1$ | $R^2$ | $R^3$ | $R^4$ |
|---|---|---|---|---|---|
| XIIa-1 | 1H NMR | $OCH_3$ | H | H | H |
| XIIa-2 | 1H NMR | H | H | H | H |
| XIIa-3 | 1H NMR | $OCH_2$-p-tolyl | H | H | H |
| XIIa-4 | 1H NMR | F | H | H | H |
| XIIa-5 | 1H NMR | $CF_3$ | H | H | H |
| XIIa-6 | 1H NMR | Cl | H | H | H |
| XIIa-7 | 1H NMR | $OCH_2CH_3$ | H | H | H |
| XIIa-8 | 1H NMR | $OCHF_2$ | H | H | H |
| XIIa-9 | | Br | H | H | H |
| XIIa-10 | | $OCF_3$ | H | H | H |
| XIIa-11 | | $SCH_3$ | H | H | H |
| XIIa-12 | | $CH_3$ | H | H | H |

XIIa-1:
$^1$H NMR: δ ([D6]-DMSO)=2.85-2.86 (d, 3H); 3.91 (s, 3H); 5.82 (br., 1H); 6.68-6.70 (m, 1H); 6.94-6.97 (m, 1H); 7.39-7.43 (m, 1H) ppm XIIa-2:
$^1$H NMR: δ ([D6]-DMSO)=2.88-2.89 (d, 3H); 6.71 (br., 1H); 7.20-7.24 (m, 1H); 7.40-7.42 (m, 1H); 7.48-7.52 (m, 1H); 7.76-7.78 (m, 1H) ppm XIIa-3:
$^1$H NMR: δ ([D6]-DMSO)=2.29 (s, 3H); 2.87 (d, 3H); 5.27 (s, 2H); 5.66 (q, 1H); 6.72-6.74 (m, 1H); 6.93-6.95 (m, 1H); 7.18-7.21 (m, 2H); 7.33-7.39 (m, 3H) ppm XIIa-4:
$^1$H NMR: δ ([D6]-DMSO)=2.86 (d, 3H); 6.36 (q, 1H); 6.97-7.02 (m, 1H); 7.28-7.30 (m, 2H); 7.50-7.55 (m, 1H) ppm XIIa-5:
$^1$H NMR: δ ([D6]-DMSO)=2.93-2.94 (d, 3H); 5.46 (q, 1H); 7.64-7.87 (m, 3H) ppm XIIa-6:
$^1$H NMR: δ ([D6]-DMSO)=2.89-2.90 (d, 3H); 6.09 (q, 1H); 7.24-7.27 (m, 1H); 7.43-7.45 (m, 1H); 7.49-7.53 (m, 1H) ppm XIIa-7:
$^1$H NMR: δ ([D6]-DMSO)=1.41 (t, 3H); 2.87-2.88 (d, 3H); 4.18-4.23 (q, 2H); 5.64 (q, 1H); 6.67-6.69 (m, 1H); 6.93-6.95 (m, 1H); 7.37-7.41 (m, 1H) ppm XIIa-8:
$^1$H NMR: δ ([D6]-DMSO)=2.88-2.89 (d, 3H); 5.91 (q, 1H); 7.13 (m, 1H); 7.30 (m, 1H); 7.31 (t, 1H); 7.52 (m, 1H) ppm Preparation of Starting Materials of the Formula (IVb)

Example 7

Preparation of 2-ethoxy-6-hydroxybenzenecarboximidamide

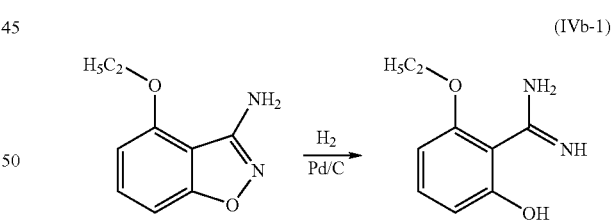
(IVb-1)

3.65 g [20.48 mmol] of 4-ethoxy-3-amino-1,2-benzisoxazole are hydrogenated in 40 ml of methanol and in the presence of 0.39 g of palladium (loading: 10, support: activated carbon) at room temperature and pressure 1 bar for 16 hours, analogously to the method from WO 2007/030582. The reaction mixture is filtered through silica gel, and rinsed through repeatedly with methanol. The combined filtrates are concentrated under reduced pressure. This leaves 1.9 g of product as a beige solid; the purity according to LC-MS is 100%.

The compounds of the general formula (IV-b) described in the table which follows are obtained according to or analogously to the above-described synthesis example:

TABLE 4 compounds of the formula (IVb)

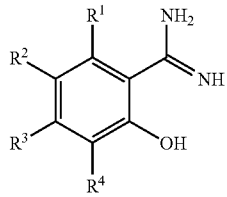

(IVb)

| No. | Phys. data | R¹ | R² | R³ | R⁴ |
|---|---|---|---|---|---|
| IVb-1 | 1H NMR | $OC_2H_5$ | H | H | H |
| IVb-2 | 1H NMR | $CF_3$ | H | H | H |
| IVb-3 | 1H NMR | F | H | H | H |
| IVb-4 | 1H NMR | $OCHF_2$ | H | H | H |
| IVb-5 | | $OCH_3$ | H | H | H |
| IVb-6 | | $OCF_3$ | H | H | H |
| IVb-7 | | $SCH_3$ | H | H | H |
| IVb-8 | | Cl | H | H | H |
| IVb-9 | | Br | H | H | H |
| IVb-10 | | $CH_3$ | H | H | H |
| IVb-11 | | H | H | H | H |

IVb-1:
$^1$H NMR: δ ([D6]-DMSO)=1.36 (t, 3H); 4.05-4.10 (q, 2H); 5.83-5.85 (m, 1H); 6.07-6.10 (m, 1H); 6.91-6.95 (m, 1H) ppm IVb-2:
$^1$H NMR: δ ([D6]-DMSO)=6.43-6.45 (m, 1H); 6.58-6.60 (m, 1H); 7.04-7.08 (m, 1H) ppm IVb-3:
$^1$H NMR: δ ([D6]-DMSO)=5.91-5.97 (m, 1H); 6.25-6.28 (m, 1H); 6.96-7.03 (m, 1H) ppm IVb-4:
$^1$H NMR: δ ([D6]-DMSO)=5.97-6.00 (m, 1H); 6.33-6.36 (m, 1H); 7.00-7.04 (m, 1H); 7.13 (t, 1H) ppm Preparation of Starting Materials of the Formula (Ivc)

Example 8

Preparation of 2-ethoxy-6-hydroxy-N-methylbenzenecarboximidamide (IVc-1)

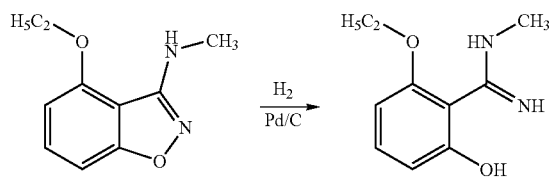

2.75 g [14.31 mmol] of 4-ethoxy-N-methyl-1,2-benzisoxazol-3-amine are hydrogenated in 30 ml of methanol and in the presence of 0.28 g of palladium (loading: 10, support: activated carbon) at room temperature and pressure 1 bar for 16 hours, analogously to the method from WO 2007/030582. The reaction mixture is filtered through silica gel, and rinsed through repeatedly with methanol. The combined filtrates are concentrated under reduced pressure. This leaves 1.1 g of product as a grey solid; the purity is >95% according to $^1$H NMR.

The compounds of the general formula (IVc) described in the table which follows are obtained according to or analogously to the above-described synthesis example:

TABLE 5 compounds of the formula (IVc)

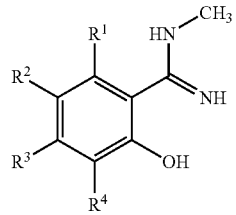

(IVc)

| No. | Phys. data | R¹ | R² | R³ | R⁴ |
|---|---|---|---|---|---|
| IVc-1 | 1H NMR | $OC_2H_5$ | H | H | H |
| IVc-2 | 1H NMR | H | H | H | H |
| IVc-3 | 1H NMR | $OCH_3$ | H | H | H |
| IVc-4 | 1H NMR | $CF_3$ | H | H | H |
| IVc-5 | 1H NMR | $OCHF_2$ | H | H | H |
| IVc-6 | | F | H | H | H |
| IVc-7 | | Cl | H | H | H |
| IVc-8 | | Br | H | H | H |
| IVc-9 | | $SCH_3$ | H | H | H |
| IVc-10 | | $OCF_3$ | H | H | H |
| IVc-11 | | $CH_3$ | H | H | H |

IVc-1:
1H NMR: δ ([D6]-DMSO)=1.37 (t, 3H); 2.90 (s, 3H); 4.08-4.13 (q, 2H); 5.93-5.95 (m, 1H); 6.13-6.15 (m, 1H); 6.92-6.96 (m, 1H) ppm IVc-2:
1H NMR: δ ([D6]-DMSO)=2.92 (s, 3H); 6.27-6.31 (m, 1H); 6.47-6.50 (m, 1H); 7.05-7.09 (m, 1H); 7.54-7.57 (m, 1H); 8.35 (br. s, 1H) ppm IVc-3:
1H NMR: δ ([D6]-DMSO)=2.89 (s, 3H); 3.81 (s, 3H); 5.92-5.93 (m, 1H); 6.13-6.16 (m, 1H); 6.94-6.97 (m, 1H) ppm IVc-4:
1H NMR: δ ([D6]-DMSO)=2.49 (d, 3H); 5.47 (q, 1H); 7.64-7.88 (m, 3H) ppm IVc-5:
1H NMR: δ ([D6]-DMSO)=2.87-2.89 (d, 3H); 5.97-6.00 (q, 1H); 6.36 (m, 1H); 7.02 (m, 1H); 7.13 (t, 1H); 7.49-7.54 (m, 1H) ppm.

APPLICATION EXAMPLES

Example No. 1

Myzus Test (MYZUPE Spray Treatment)

Solvent: 78.0 parts by weight of acetone 1.5 parts by weight of dimethylformamide Emulsifier: 0.5 part by weight of alkylaryl polyglycol ether To prepare an appropriate preparation of active ingredient, 1 part by weight of active ingredient is mixed with the stated amounts of solvents and emulsifier, and the concentrate is diluted with emulsifier-containing water to the desired concentration.

Discs of Chinese cabbage (*Brassica pekinensis*) infected by all stages of the green peach aphid (*Myzus persicae*) are sprayed with an active ingredient preparation of the desired concentration.

After the desired time, the effect in % is determined. 100% means that all of the aphids have been killed; 0% means that none of the aphids have been killed.

In this test, for example, the following compounds from the Preparation Examples show, at an application rate of 500 g/ha, an effect of ≧80%:
Ex. No. I-1, I-3, I-4

Example No. 2

*Ctenocephalides felis*; Oral (CTECFE)
Solvent: 1 part by weight of dimethyl sulphoxide For the purpose of preparing an appropriate preparation of active ingredient, 2 parts by weight of active ingredient are mixed with the stated amount of solvent. Part of the concentrate is diluted with citrated cattle blood, and the desired concentration is prepared.

20 unfed adult fleas (*Ctenocephalides felis*) are placed into a chamber closed at the top and bottom with gauze. A metal cylinder whose bottom end is closed with parafilm is placed onto the chamber. The cylinder contains the blood/active ingredient preparation, which can be taken up by the fleas through the parafilm membrane.

After the desired time, the kill in % is determined. 100% means that all fleas have been killed; 0% means that none of the fleas have been killed.

In this test, for example, the following compound from the Preparation Examples shows, at an application rate of 100 ppm, an effect of ≧80%:
Ex. No. I-4

Example No. 3

*Boophilus microplus* Test (BOOPMI Injection)
Solvent: dimethyl sulphoxide

To prepare an appropriate preparation of active ingredient, 1 part by weight of active ingredient is mixed with the stated amount of solvent, and the concentrate is diluted with water to the desired concentration.

The solution of active ingredient is injected into the abdomen (*Boophilus microplus*), and the animals are transferred into dishes and kept in a temperature-controlled room. The effect is assessed by the laying of fertile eggs.

After the desired time, the effect in % is determined. 100% means that no tick has laid any fertile eggs.

In this test, for example, the following compound from the Preparation Examples shows, at an application rate of 20 µg/animal, an effect of ≧80%:
Ex. No. I-1

The invention claimed is:
1. Compounds of the formula (I)

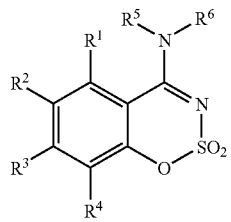

(I)

in which
$R^1$, $R^2$, $R^3$ and $R^4$ are each independently selected from the group consisting of
hydrogen, halogen, carbamoyl, thiocarbamoyl, nitro, cyano, hydroxyl, $SF_5$, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_6$-alkoxy, $C_1$-$C_6$-alkoxycarbonyl, $C_3$-$C_6$-alkenyloxy, $C_3$-$C_6$-cycloalkyloxy, $C_3$-$C_6$-cycloalkyloxy-$C_1$-$C_4$-alkyl, $C_1$-$C_4$-alkoxy-$C_1$-$C_4$-alkyl, aryloxy, hetaryloxy, aryl-$C_1$-$C_4$-alkyloxy, hetaryl-$C_1$-$C_4$-alkyloxy, O-acetyl, ($C_1$-$C_4$-alkyl)amino, di-($C_1$-$C_4$-alkyl)amino, $C_3$-$C_6$-trialkylsilyl, aryl, hetaryl, aryl-$C_1$-$C_6$-alkyl and hetaryl-$C_1$-$C_6$-alkyl, where these radicals may be unsubstituted or may bear one, two or more radicals selected from the group consisting of
halogen, cyano, $C_1$-$C_6$-alkyl, $C_3$-$C_8$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;

$R^5$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_8$-alkyl, $C_3$-$C_6$-cycloalkyl, $C_2$-$C_6$-alkenyl, $C_1$-$C_4$-alkoxy, $C_1$-$C_4$-alkylthio, $C_1$-$C_4$-alkylsulphinyl, $C_1$-$C_4$-alkylsulphonyl, aryl, hetaryl, aryl-$C_1$-$C_6$-alkyl, hetaryl-$C_1$-$C_6$-alkyl and —(C=X)NR$^7$R$^{7'}$, where these radicals may be unsubstituted or may bear one, two or more radicals selected from the group consisting of
halogen, cyano, $C_1$-$C_6$-alkyl, $C_3$-$C_8$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;

$R^6$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_8$-alkyl, $C_3$-$C_6$-cycloalkyl, $C_2$-$C_6$-alkenyl, $C_1$-$C_4$-alkylsulphinyl, $C_1$-$C_4$-alkylsulphonyl, aryl, hetaryl, aryl-$C_1$-$C_6$-alkyl, hetaryl-$C_1$-$C_6$-alkyl and —(C=X)NR$^7$R$^{7'}$, where these radicals may be unsubstituted or may bear one, two or more radicals selected from the group consisting of
halogen, cyano, $C_1$-$C_6$-alky, $C_3$-$C_8$-cycloalkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;

provided that $R^5$, $R^6$ together are not phenylbutyl and hydrogen if $R^1$ is methoxy; and
$R^1$, $R^2$, $R^3$, $R^4$ radicals are not all hydrogen if $R^5$ and $R^6$ are each hydrogen;
$R^7$ is selected from the group consisting of $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, aryl, and hetaryl,
where these radicals may be unsubstituted or may bear one, two or more radicals selected from the group consisting of
halogen, cyano, nitro, $C_1$-$C_6$-alkyl, $C_3$-$C_6$-cycloalkyl, $C_1$-$C_6$-alkoxy, $C_1$-$C_6$-haloalkyl, and $C_1$-$C_6$-haloalkoxy;
$R^{7'}$ is selected from the group consisting of hydrogen, $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, aryl, and hetaryl, where these radicals may be unsubstituted or may bear one, two or more radicals selected from the group consisting of halogen, cyano, nitro, $C_1$-$C_6$-alkyl, $C_3$-$C_6$-cycloalkyl, $C_1$-$C_6$-alkoxy, $C_1$-$C_6$-haloalkyl, and $C_1$-$C_6$-haloalkoxy;

X is O, or S, and salts of compounds of the formula (I).

2. Compounds of the formula (I) according to claim 1, where $R^1$, $R^2$, $R^3$ and $R^4$ are each independently selected from the group consisting of hydrogen, halogen, cyano, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_4$-alkylthio, $C_1$-$C_4$-haloalkyl, $C_1$-$C_4$-alkylcarbonyl, $C_1$-$C_6$-alkoxy, $C_1$-$C_6$-alkoxycarbonyl, $C_3$-$C_6$-alkenyloxy, $C_3$-$C_6$-cycloalkyloxy, $C_3$-$C_6$-cycloalkyloxy-$C_1$-$C_4$-alkyl, $C_1$-$C_4$-haloalkoxy, $C_1$-$C_4$-alkoxy-$C_1$-$C_4$-alkyl, O-acetyl, aryl, hetaryl, aryl-$C_1$-$C_6$-alkyl, hetaryl-$C_1$-$C_6$-alkyl, and from optionally $C_1$-$C_6$-alkyl-substituted aryloxy, hetaryloxy, aryl-$C_1$-$C_4$-alkyloxy, and hetaryl-$C_1$-$C_4$-alkyloxy, provided that $R^1$, $R^2$, $R^3$ and $R^4$ radicals are not all hydrogen if $R^5$ and $R^6$ are hydrogen;

$R^5$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_6$-alkyl, $C_3$-$C_6$-cycloalkyl, $C_2$-$C_6$-alkenyl, $C_1$-$C_4$-alkoxy, $C_1$-$C_4$-haloalkyl, $C_1$-$C_4$-haloalkoxy, aryl, hetaryl, aryl-$C_1$-$C_2$-alkyl, hetaryl-$C_1$-$C_2$-alkyl, ($C_1$-$C_4$-haloalkyl)carbonyl, and —(C=X)$NR^7R^{7'}$, $R^6$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_6$-alkyl, $C_3$-$C_6$-cycloalkyl, $C_2$-$C_6$-alkenyl, $C_1$-$C_4$-haloalkoxy, aryl, hetaryl, aryl-$C_1$-$C_2$-alkyl, hetaryl-$C_1$-$C_2$-alkyl, ($C_1$-$C_4$-haloalkyl)carbonyl, and —(C=X)$NR^7R^{7'}$, $R^7$ is selected from the group consisting of $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl, thiophene, and furan, where these radicals may be unsubstituted or may bear one, two or more radicals selected from the group consisting of halogen, cyano, nitro, $C_1$-$C_4$-alkyl, $C_3$-$C_4$-cycloalkyl, $C_1$-$C_4$-alkoxy, $C_1$-$C_4$-haloalkyl, and $C_1$-$C_4$-haloalkoxy;

$R^{7'}$ is selected from the group consisting of hydrogen, $C_1$-$C_4$-alkyl, $C_3$-$C_4$-cycloalkyl, $C_1$-$C_4$-alkoxy, $C_1$-$C_4$-haloalkyl, $C_1$-$C_4$-haloalkoxy, phenyl, pyridyl, thiophene, and furan, where these radicals may be unsubstituted or may bear one, two or more radicals selected from the group consisting of halogen, cyano, nitro, $C_1$-$C_4$-alkyl, $C_3$-$C_4$-cycloalkyl, $C_1$-$C_4$-alkoxy, $C_1$-$C_4$-haloalkyl, and $C_1$-$C_4$-haloalkoxy; and X is O.

3. Composition comprising at least one compound of the formula (I) according to claim 1 and at least one salt of the formula (IX)

$$\left[ R^{11}-\underset{\underset{R^{10}}{|}}{\overset{\overset{R^8}{|}}{D^+}}-R^9 \right]_m R^{12\,m-},\qquad \text{(IX)}$$

in which

D is nitrogen or phosphorus, $R^8$, $R^9$, $R^{10}$ and $R^{11}$ are each independently hydrogen or in each case optionally substituted $C_1$-$C_8$-alkyl or mono- or polyunsaturated, optionally substituted $C_1$-$C_8$-alkylene, where the substituents may be halogen, nitro or cyano, m is 1, 2, 3 or 4, and $R^{12}$ is an inorganic or organic anion.

4. Composition comprising at least one compound of the formula (I) according to claim 1 and at least one penetrant of the formula (X)

$$R\text{—}O\text{—}(\text{-AO})_v\text{—}R' \qquad \text{(X)}$$

in which

R is straight-chain or branched alkyl having 4 to 20 carbon atoms,

R' is hydrogen, methyl, ethyl, n-propyl, i-propyl, n-butyl, i-butyl, t-butyl, n-pentyl or n-hexyl, AO is an ethylene oxide radical, a propylene oxide radical, a butylene oxide radical or mixtures of ethylene oxide and propylene oxide radicals or butylene oxide radicals, and v is from 2 to 30.

5. Composition according to claim 3 or comprising at least one compound of the formula (I), at least one salt of the formula (IX) and at least one penetrant of the formula (X):

$$R\text{—}O\text{—}(\text{-AO})_v\text{—}R' \qquad \text{(X)}$$

in which

R is straight-chain or branched alkyl having 4 to 20 carbon atoms,

R' is hydrogen, methyl, ethyl, n-propyl, i-propyl, n-butyl, i-butyl, t-butyl, n-pentyl or n-hexyl, AO is an ethylene oxide radical, a propylene oxide radical, a butylene oxide radical or mixtures of ethylene oxide and propylene oxide radicals or butylene oxide radicals, and v is from 2 to 30.

6. Process for preparing compounds of the formula (I) according to claim 1, characterized in that (A) 2-cyanophenyloxysulphonamides of the formula (II)

(II)

[Structure: benzene ring with $R^1$, $R^2$, $R^3$, $R^4$ substituents, a CN group, and an O—$SO_2NH_2$ group]

in which $R^1$, $R^2$, $R^3$ and $R^4$ are each as defined above, are cyclized in the presence of ultrasound-pretreated baker's yeast to give compounds of the formula (I) in which $R^1$, $R^2$, $R^3$ and $R^4$ are each as defined above and $R^5$ and $R^6$ are each hydrogen;
or
(B) 2-cyanophenols of the formula (III)

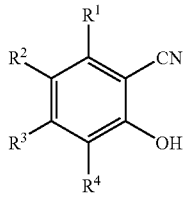
(III)

in which $R^1$, $R^2$, $R^3$ and $R^4$ are each as defined above, are reacted with chlorosulphonyl isocyanate to give 2-cyanophenyloxysulphonamides of the formula (II)

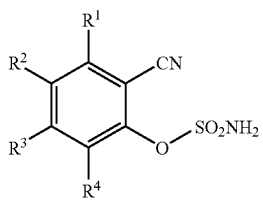
(II)

in which $R^1$, $R^2$, $R^3$ and $R^4$ are each as defined above,
and the latter are cyclized without isolation in a one-pot reaction to give compounds of the formula (I) in which $R^1$, $R^2$, $R^3$ and $R^4$ are each as defined above and $R^5$ and $R^6$ are each hydrogen;
or
(C) 2-amidinophenols of the formula (IV)

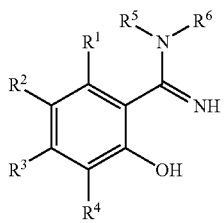
(IV)

in which $R^1$, $R^2$, $R^3$, $R^4$, $R^5$, and $R^6$ are each as defined above,
are reacted with a sulphonyl derivative of the formula (V),

(V)

where X, Y are each halogen, pyrazole, triazole, or imidazole,
to give compounds of the formula (I) in which $R^1$, $R^2$, $R^3$, $R^4$, $R^5$, and $R^6$ are each as defined above;

or
(D) compounds of the formula (Ib)

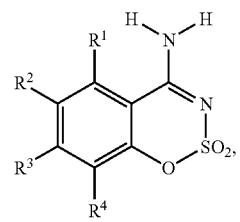
(Ib)

in which $R^1$, $R^2$, $R^3$, $R^4$ are each as defined above, are reacted with compounds of the formula (VI)

$$Z-R^5 \quad (VI)$$

where
$R^5$ is as defined above,
Z is a leaving group selected from the group consisting of halide, sulphonate, thiocarboxylate, and carboxylate, to give compounds of the formula (Ic)

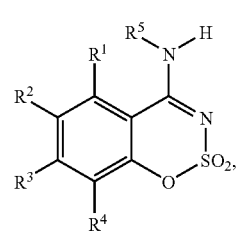
(Ic)

and/or compounds of the formula (Ib) or (Ic),
in which $R^1$, $R^2$, $R^3$, $R^4$, $R^5$ are each as defined above, are reacted with compounds of the formula (VII)

$$Z-R^6 \quad (VII)$$

where
Z, and $R^6$ are each as defined above,
to give compounds of the formula (I);
or
(E) compounds of the formula (Ic)
in which $R^1$, $R^2$, $R^3$, $R^4$, and $R^5$ are each as defined above, are reacted with iso(thio)cyanates of the formula (VIII)

$$R^7-N=C=X \quad (VIII)$$

in which X, $R^7$ are each as defined above,
to give compounds of the formula (Ie) in which $R^1$, $R^2$, $R^3$, $R^4$ and $R^5$ are each as defined above and $R^6$ is a monosubstituted amino(thio)carbonyl radical

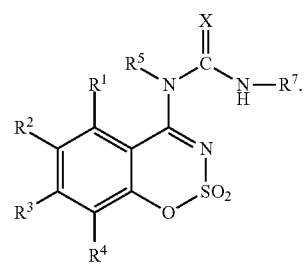
(Ie)

7. Method for controlling animal pests, characterized in that compounds of the formula (I) according to claim 1 are allowed to act on animal pests and/or phytopathogenic fungi and/or the habitat thereof and/or seed and/or plant propagation material and/or plant parts which form later from plant propagation material.

8. Process for producing agrochemical compositions, characterized in that compounds of the formula (I) according to claim 1 are mixed with extenders and/or surfactants.

9. A method for controlling pests in crop protection, in industrial material protection, in the veterinary sector, and combinations thereof, comprising treating a crop plant or its parts, an industrial material which is selected from the group consisting of plastics, adhesives, sizes, papers and cards, leather, wood and processed wood products and coating compositions, or an animal with a compound of formula (I):

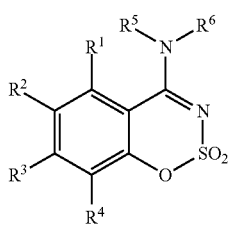

(I)

in which $R^1$, $R^2$, $R^3$, and $R^4$ are each independently selected from the group consisting of hydrogen, halogen, carbamoyl, thiocarbamoyl, nitro, cyano, hydroxyl, $SF_5$, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_6$-alkoxy, $C_1$-$C_6$-alkoxycarbonyl, $C_3$-$C_6$-alkenyloxy, $C_3$-$C_6$-cycloalkyloxy, $C_3$-$C_6$-cycloalkyloxy-$C_1$-$C_4$-alkyl, $C_1$-$C_4$-alkoxy-$C_1$-$C_4$-alkyl, aryloxy, hetaryloxy, aryl-$C_1$-$C_4$-alkyloxy, hetaryl-$C_1$-$C_4$-alkyloxy, O-acetyl, ($C_1$-$C_4$-alkyl)amino, di-($C_1$-$C_4$-alkyl)amino, $C_3$-$C_6$-trialkylsilyl, aryl, hetaryl, aryl-$C_1$-$C_6$-alkyl and hetaryl-$C_1$-$C_6$-alkyl, where these radicals may be unsubstituted or may bear one, two or more radicals selected from the group consisting of halogen, cyano, $C_1$-$C_6$-alkyl, $C_3$-$C_8$-cycloalkyl, $C_1$-$C_4$-alkoxy, $C_1$-$C_4$-alkylthio, $C_1$-C4-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;

$R^5$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_8$-alkyl, $C_3$-$C_6$-cycloalkyl, $C_2$-$C_6$-alkenyl, $C_1$-$C_4$-alkoxy, $C_1$-$C_4$-alkylthio, $C_1$-$C_4$-alkylsulphinyl, $C_1$-$C_4$-alkylsulphonyl, aryl, hetaryl, aryl-$C_1$-$C_6$-alkyl, hetaryl-$C_1$-$C_6$-alkyl and —(C=X)$NR^7R^{7'}$, where these radicals may be unsubstituted or may bear one, two or more radicals selected from the group consisting of halogen, cyano, $C_1$-$C_6$-alkyl, $C_3$-$C_8$-cycloalkyl, $C_1$-$C_4$-alkoxy, $C_1$-$C_4$-alkylthio, $C_1$-C4-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;

$R^6$ is selected from the group consisting of hydrogen, ($C_1$-$C_6$-alkyl)carbonyl, ($C_1$-$C_6$-alkoxy)carbonyl, ($C_1$-$C_6$-alkylthio)carbonyl, ($C_1$-$C_6$-alkyl)thiocarbonyl, ($C_1$-$C_6$-alkoxy)thiocarbonyl, ($C_1$-$C_6$-alkylthio)thiocarbonyl, $C_1$-$C_8$-alkyl, $C_3$-$C_6$-cycloalkyl, $C_2$-$C_6$-alkenyl, $C_1$-$C_4$-alkylsulphinyl, $C_1$-$C_4$-alkylsulphonyl, aryl, hetaryl, aryl-$C_1$-$C_6$-alkyl, hetaryl-$C_1$-$C_6$-alkyl and —(C=X)$NR^7R^{7'}$, where these radicals may be unsubstituted or may bear one, two or more radicals selected from the group consisting of halogen, cyano, $C_1$-$C_6$-alkyl, $C_3$-$C_8$-cycloalkyl, $C_1$-$C_4$-alkoxy, $C_1$-$C_4$-alkylthio, $C_1$-C4-alkylsulphinyl, $C_1$-$C_4$-alkylsulphonyl, $C_1$-$C_4$-haloalkyl, $C_1$-$C_4$-haloalkoxy, $C_1$-$C_4$-haloalkylthio, ($C_1$-$C_4$-alkyl)amino, di-($C_1$-$C_4$-alkyl)amino, aryl and hetaryl;

provided that $R^5$, $R^6$ together are not phenylbutyl or hydrogen if $R^1$ is methoxy;

$R^7$ is selected from the group consisting of $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, aryl, and hetaryl, where these radicals may be unsubstituted or may bear one, two or more radicals selected from the group consisting of halogen, cyano, nitro, $C_1$-$C_6$-alkyl, $C_3$-$C_6$-cycloalkyl, $C_1$-$C_6$-alkoxy, $C_1$-$C_6$-haloalkyl, and $C_1$-$C_6$-haloalkoxy;

$R^{7'}$ is selected from the group consisting of hydrogen, $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, aryl, and hetaryl, where these radicals may be unsubstituted or may bear one, two or more radicals selected from the group consisting of halogen, cyano, nitro, $C_1$-$C_6$-alkyl, $C_3$-$C_6$-cycloalkyl, $C_1$-$C_6$-alkoxy, $C_1$-$C_6$-haloalkyl, and $C_1$-$C_6$-haloalkoxy;

X is O, or S.

10. A method for controlling animal pests, characterized in that a composition according to claim 3 is allowed to act on animal pests and/or phytopathogenic fungi and/or the habitat thereof and/or seed and/or plant propagation material and/or plant parts which form later from plant propagation material.

11. A method for controlling animal pests, characterized in that a composition according to claim 4 is allowed to act on animal pests and/or phytopathogenic fungi and/or the habitat thereof and/or seed and/or plant propagation material and/or plant parts which form later from plant propagation material.

12. A method for controlling animal pests, characterized in that a composition according to claim 5 is allowed to act on animal pests and/or phytopathogenic fungi and/or the habitat thereof and/or seed and/or plant propagation material and/or plant parts which form later from plant propagation material.

* * * * *